(12) United States Patent
Fishman et al.

(10) Patent No.: US 11,894,123 B2
(45) Date of Patent: Feb. 6, 2024

(54) RADIOTHERAPY MOBILE AND WIRELESS DEVICE WORKFLOW MANAGEMENT SYSTEM

(71) Applicant: Sensus Healthcare, Inc., Boca Raton, FL (US)

(72) Inventors: Kalman Fishman, Boca Raton, FL (US); Yonatan Vainer, Boca Raton, FL (US)

(73) Assignee: SENSUS HEALTHCARE, INC., Boca Raton, FL (US)

( * ) Notice: Subject to any disclaimer, the term of this patent is extended or adjusted under 35 U.S.C. 154(b) by 441 days.

(21) Appl. No.: 15/946,544

(22) Filed: Apr. 5, 2018

(65) Prior Publication Data

US 2018/0294052 A1  Oct. 11, 2018

Related U.S. Application Data

(60) Provisional application No. 62/481,963, filed on Apr. 5, 2017.

(51) Int. Cl.
*G16H 20/40* (2018.01)
*G16H 10/65* (2018.01)
(Continued)

(52) U.S. Cl.
CPC ......... *G16H 20/40* (2018.01); *G06Q 10/1095* (2013.01); *G06T 5/50* (2013.01);
(Continued)

(58) Field of Classification Search
None
See application file for complete search history.

(56) References Cited

U.S. PATENT DOCUMENTS 5,892,238 A  4/1999 Huttner et al.
2005/0065421 A1  3/2005 Burckhardt
(Continued)

FOREIGN PATENT DOCUMENTS

WO  2013106794 A2  7/2013
WO  2016064750 A1  4/2016

OTHER PUBLICATIONS

International Search Report dated Sep. 25, 2017 in PCT/US2017/027715.
(Continued)

*Primary Examiner* — Rajesh Khattar
*Assistant Examiner* — Andrew E Lee
(74) *Attorney, Agent, or Firm* — Fox Rothschild LLP

(57) ABSTRACT

Systems and methods for treating a patient. The methods comprise: producing, by a radiotherapy system, a fused model for a superficial portion of the patient's skin by combining structural imaging data acquired using high frequency ultrasound and functional imaging data acquired using optical imaging; generating a treatment plan for the patient based on the fused model; storing the treatment plan; detecting, by a processor, an arrival of the patient at a medical facility using first information acquired from a first mobile device coupled to the patient; obtaining the treatment plan using the first information; and causing a state of medical equipment to be transitioned from a first configurable operational state in which a radiotherapy treatment head has a first position to a second configurable operational state in which the radiotherapy treatment head has a second different position, in accordance with the treatment plan.

33 Claims, 17 Drawing Sheets

(51) Int. Cl.
    *G06Q 10/1093*     (2023.01)
    *G06T 5/50*        (2006.01)
    *G16H 50/20*       (2018.01)
    *G16H 30/20*       (2018.01)
    *G16H 40/20*       (2018.01)
    *G16H 30/40*       (2018.01)
    *G16H 40/60*       (2018.01)
    *H04W 4/029*       (2018.01)
    *H04W 4/021*       (2018.01)
    *H04W 4/80*        (2018.01)
    *A61N 5/10*        (2006.01)
    *H04W 4/90*        (2018.01)

(52) U.S. Cl.
    CPC ............. *G16H 10/65* (2018.01); *G16H 30/20* (2018.01); *G16H 30/40* (2018.01); *G16H 40/20* (2018.01); *G16H 40/60* (2018.01); *G16H 50/20* (2018.01); *A61N 5/103* (2013.01); *A61N 2005/1074* (2013.01); *G06T 2207/20221* (2013.01); *H04W 4/021* (2013.01); *H04W 4/029* (2018.02); *H04W 4/80* (2018.02); *H04W 4/90* (2018.02)

(56) References Cited

U.S. PATENT DOCUMENTS

| | | | | |
|---|---|---|---|---|
| 2006/0277074 A1* | 12/2006 | Einav | ............. | G06Q 50/24 |
| | | | | 705/3 |
| 2008/0002811 A1* | 1/2008 | Allison | ............... | A61N 5/1049 |
| | | | | 378/65 |
| 2008/0131362 A1* | 6/2008 | Rousso | ............... | A61M 5/1785 |
| | | | | 424/1.11 |
| 2008/0275741 A1* | 11/2008 | Loeffen | ............. | G06Q 10/1095 |
| | | | | 705/5 |
| 2009/0206992 A1* | 8/2009 | Giobbi | ................... | G16H 10/60 |
| | | | | 340/5.74 |
| 2011/0137177 A1 | 6/2011 | Toma et al. | | |
| 2013/0188856 A1* | 7/2013 | Adler, Jr. | ............... | A61N 5/107 |
| | | | | 382/132 |
| 2013/0217947 A1* | 8/2013 | Fishman | ............. | A61N 5/1049 |
| | | | | 600/1 |
| 2015/0159994 A1 | 6/2015 | Hofmann et al. | | |
| 2016/0004820 A1 | 1/2016 | Moore | | |
| 2016/0008629 A1* | 1/2016 | Ribbing | ............... | A61N 5/103 |
| | | | | 435/7.92 |
| 2016/0104312 A1 | 4/2016 | Zino et al. | | |
| 2018/0294052 A1 | 10/2018 | Fishman | | |

OTHER PUBLICATIONS

International Search Report dated Jun. 28, 2018 in PCT/US2018/026304.

* cited by examiner

RADIOTHERAPY MOBILE AND WIRELESS DEVICE WORKFLOW MANAGEMENT SYSTEM

CROSS REFERENCE TO RELATED APPLICATIONS

This application claims the benefit of U.S. Patent Provisional Application No. 62/481,963, filed on Apr. 5, 2017. This Provisional Application is hereby incorporated by reference in its entirety.

FIELD

The present disclosure relates to systems, devices and methods for managing workflow in a medical facility. More particularly, the present disclosure relates to radiotherapy mobile and wireless device workflow management system and methods.

BACKGROUND

In the field of radiation oncology, accurate imaging is an important component of treating cancer. Images which combine imaging information acquired using different imaging technologies are sometimes referred to as hybrid images. For, example Positron Emission Tomography ("PET") is used to image many common types of cancers. Imaging data from PET scanning can be used in combination with other types of imaging data to help treatment specialists more fully understand details of a malignancy. For example, image data from PET scanning can be combined with X-ray Computed Tomography ("CT") type scanning.

Once the nature of a cancer is understood by using the appropriate imaging methods, a radiation treatment plan can be determined by a medical practitioner. The treatment plan is usually based on the mass of the tumor, the location, angles of attack which may be used for radiation therapy, how much radiation energy should be applied and so on. There is existing Radiation Therapy Planning ("RTP") equipment for this purpose which is made by various manufacturers.

Skin cancer is a type of cancer in which an abnormal growth of cells appears in the skin, and is the most commonly diagnosed type of cancer. The three (3) most common malignant skin cancers are basal cell cancer, squamous cell cancer, and melanoma, each of which is named after the type of skin cell from which it arises. The chances of surviving skin cancer increase if it is detected early and treated appropriately.

For the most part, skin cancer is viewed as a simpler problem than other types of cancer. Since it often appears directly on the surface of the skin, it is thought of as more of a two-dimensional ("2D") problem as opposed to a three-dimensional ("3D") problem as in other types of cancer. So unlike other types of cancers, skin cancers are frequently treated without the use of advanced imaging equipment. Practitioners frequently begin evaluating skin cancers by directly observing the lesion on the surface of the skin, and making an evaluation of what type of cancer might be present based on the appearance of the lesion. The practitioner may then perform a biopsy of the lesion. When the results of the biopsy are obtained at some later date, the practitioner may estimate a margin and depth of skin that must be excised to remove the lesion by surgical or other means. All this is done basically on a visual basis. In other words, there is no true treatment planning facility equivalent to what is done in the radiology field. Unfortunately, this approach to cutaneous oncology can lead to errors with regard to optimal treatment. This suboptimal treatment is in part due to the fact that skin cancer is not approached and quantified like other cancers—even though it is the most prevalent.

SUMMARY

The present disclosure concerns systems and methods for treating a patient. The methods comprise: producing, by a radiotherapy system, a fused model for a least a portion of the region of interest comprising a superficial portion of a patient's skin by combining (a) structural imaging data acquired using high frequency ultrasound and (b) functional imaging data acquired using optical imaging; generating a treatment plan for the patient based on the fused model; storing the treatment plan in a datastore; detecting, by a processor (e.g., implemented in a centralized or distributed fashion by one or more computing devices), an arrival of the patient at a medical facility using first information acquired from a first mobile device (e.g., a wearable device) coupled to the patient; obtaining, by the processor, the treatment plan for the patient from the datastore using the first information; and causing, by the processor, a state of medical equipment (e.g., an ultrasound guided radio therapy treatment and diagnosis system) to be transitioned from a first configurable operational state in which a radiotherapy treatment head has a first position to a second configurable operational state in which the radiotherapy treatment head has a second different position, in accordance with the treatment plan.

In some scenarios, the methods also comprise: communicating a notification message indicating the patient's arrival at the medical facility from the processor to a communication device coupled to or in proximity to a medical professional; tracking the patient's movement through the medical facility; generating a map showing the patient's location and/or movement through the medical facility; and presenting the map to the patient and/or a medical professional. The patient's location can be determined using beacons having known locations, via Geofencing and/or in accordance with other techniques.

In those or other scenarios, the first configurable operational state comprises a state in which radiation of a first dosage is to be applied to a person for a first amount of time. The second configurable operational state comprises a state in which radiation of a second dosage different from the first dosage is to be applied to the person or another person for a second amount of time different from the first amount of time.

In those or other scenarios, the methods further comprise: automatically acquiring at least one of appointment information and medical related information for the patient from a remote datastore in response to the detection of the patient's arrival at the medical facility; and presenting at least one of the appointment information and medical related information to the patient via the mobile device (e.g., a wearable device) or a medical professional via a communication device coupled thereto or in proximity thereto.

In those or yet other scenarios, the methods comprise: performing operations by the processor to track progress of the patient's treatment; periodically or continuously updating the patient's medical record as the patient receives treatment at the medical facility; updating the patient's medical record upon completion of the treatment; scheduling or reminding the patient of a next appointment; notifying a medical professional of the patient's next appointment so that the treatment plan is modified prior to the patient's arrival once again at the medical facility; and/or detecting a status of the medical equipment and communicating information specifying the status to a communication device of a service engineer on an hourly, daily or weekly basis.

BRIEF DESCRIPTION OF THE DRAWINGS

Embodiments will be described with reference to the following drawing figures, in which like numerals represent like items throughout the figures.

DETAILED DESCRIPTION

Figure 1:
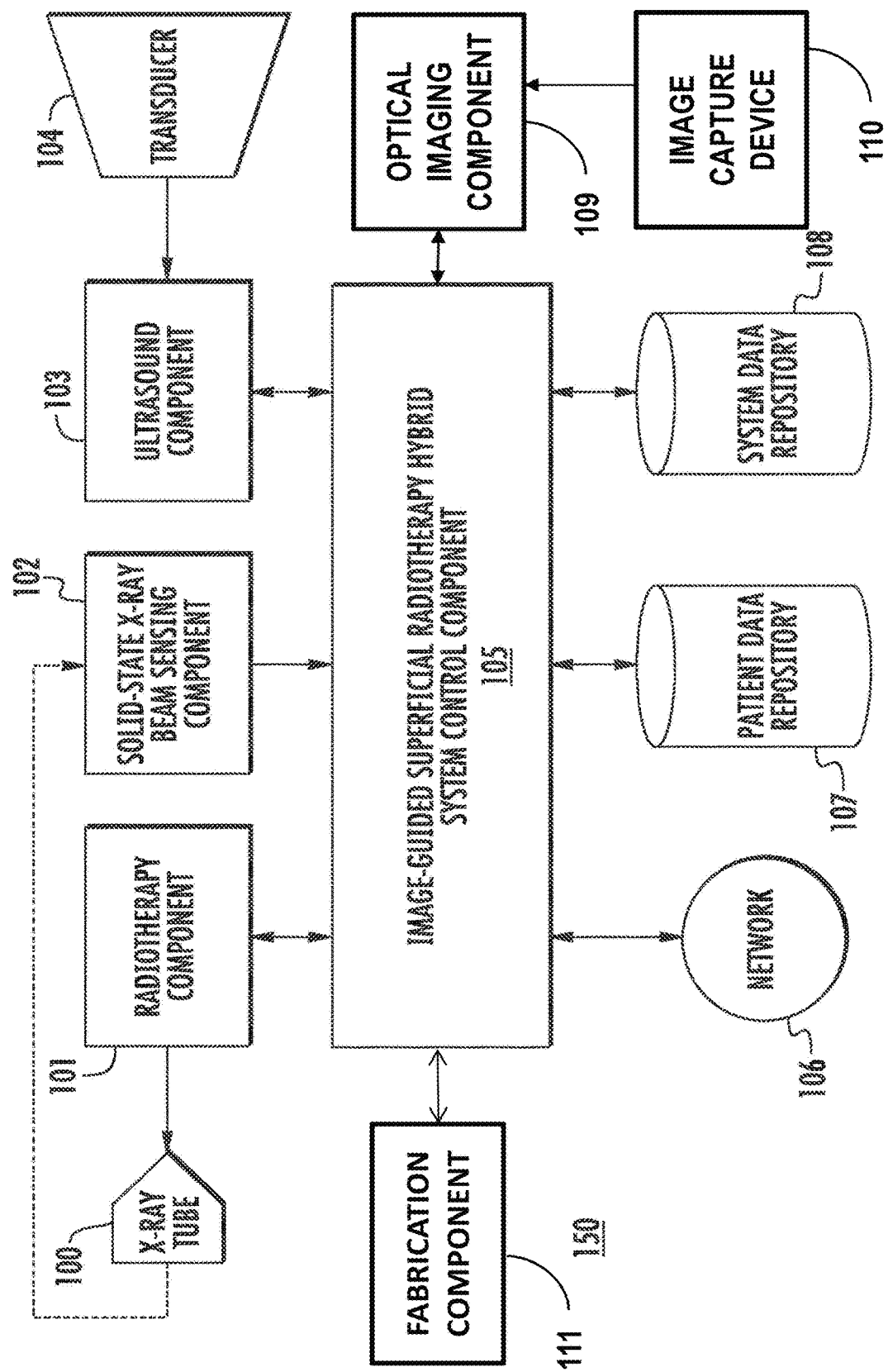
FIG. 1 is a schematic of a high level overview of the components of the system and used in the methods described herein.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

As noted above, the disclosure relates to systems, devices and methods for detecting and treating skin conditions such as skin cancers; more particularly it relates to detection of skin cancers and superficial radiotherapy treatment thereof. In particular, the present disclosure is directed to a system for dermatological radiotherapy system with a hybrid imager.

A hybrid imaging methodology disclosed herein includes a first imaging methodology that is optimal for imaging structural/anatomical features associated with a particular cutaneous lesion or malignancy, and a second imaging methodology that is optimal for obtaining functional or metabolic features associated with the cutaneous lesion. The imaging modalities are registered and fused to form a hybrid image that combines the best features of both the first and second imaging methodology.

According to one aspect, the first imaging methodology which is used is high frequency ultrasound ("HFU"). HFU is used to give the anatomical imaging modality for viewing very fine and thin tissue. The HFU imaging involves the acquisition of imaging data in a series of two-dimensional (2-D) slices which extend from the outer surface of the skin tissue toward one or more subcutaneous skin layers. A plurality of slices obtained in this way can be combined to render a three-dimensional (3-D) model of the imaged tissue volume. The volume in the areas between the 2-D slices can be extrapolated from the data associated with adjacent slices.

An HFU imaging component capable of generating 2-D slices as described herein is known in the art and therefore will not be described here in detail. However, a brief explanation of the HFU imaging modality implemented by such systems is provided to facilitate an understanding of certain embodiments described herein. When an HFU sound wave is incident on an interface between two tissues, a portion of the sound is reflected back into the original medium as a result of differences in acoustic impedance as between the two tissues. Increased differences in impedance as between tissues forming the interface will result more acoustic energy being reflected at the interface. As is known, acoustic impedance is a property of a tissue defined as density of tissue and velocity of sound in that tissue. So the HFU imaging system captures information concerning structure and density of imaged cells at different skin depths. More particularly, the HFU imaging modality can facilitate differentiation of cells based on their density. Cells in skin tissue that are associated with a lesion will have a different density as compared to healthy cells. Accordingly, the location and boundaries of a lesion can be identified in an image using the HFU imaging modality.

The HFU imaging modality can identify the presence of a lesion and its boundaries but can be inadequate to identify the biological nature of the lesion. For example, the HFU imaging modality can be inadequate to identify whether a particular lesion is a basal cell carcinoma (BCC), a squamous cell carcinoma (SCC) or a melanoma. The HFU can also be inadequate to differentiate between a skin cancer of some type and a mole or macule. In order to overcome this limitation, a second imaging methodology is used.

The second imaging methodology is an optical imaging method advantageously selected to facilitate the visualization of functional data associated with the cells which are being imaged. According to one aspect, the optical imaging methodology can be chosen to facilitate the optical acquisition of a two-dimensional image at one or more different skin depths. Accordingly, functional imaging data for a particular skin cancer can be acquired at a surface of the skin and/or at one or more different subcutaneous layers or depths beneath the surface of the skin.

According to one aspect, the optical imaging methodology is a spectroscopic imaging method. For example, the optical imaging methodology can comprise a multispectral imaging method that captures image data at a plurality of optical frequencies. Such multispectral imaging can include optical energy from the visible portion of the light spectrum but can also include optical energy from frequencies beyond the visible light range (e.g. infrared and near ultraviolet). Alternatively, the optical imaging methodology can comprise hyperspectral imaging wherein optical information is captured from across the electromagnetic spectrum at each pixel in the captured image. As a further alternative, the spectroscopic imaging method can comprise Raman spectroscopy which captures changes in the frequency of photons in monochromatic light which result from interaction with skin tissue.

The nature of a particular skin lesion will be consistent throughout the lesion, so it is not necessary to capture the functional data associated with the cells at all depths. Once the type of cancer has been determined using the second imaging methodology, all of the cells which are identified as being associated with the lesion can be marked accordingly. As noted above, the UHF imaging can differentiate such cells as having a density different from adjacent healthy/normal skin cells. Accordingly, in a subsequent data fusion process, the cells having a first density associated with a cancerous lesion can be highlighted, marked or otherwise displayed in a certain way to differentiate them from the adjacent healthy skin cells. For example, the cancerous skin cells can be displayed in a different color as compared to normal skin cells.

More particularly, the second imaging methodology described herein can be configured so that normal healthy skin cells are presented in a first color in displayed images which are presented to a user. For example, normal cells can be displayed in a green color. Cancerous cells can be presented in a different color from healthy cells. The particular color of the cancerous cells can correspond to the type of cancer which has been imaged. For example, BCC cells could be presented in yellow, SCC cells could appear blue, and melanoma cells could be presented in red.

The imaging data acquired using the first and second imaging methodology is provided to a computer workstation, such as a radiation therapy planning (RTP) workstation. Thereafter, within the RTP workstation the HFU imaging and the optical imaging is registered and then combined or superimposed to obtain a hybrid image or a fused model. The workstation will use the images from the first and second image source to create a hybrid HFU/optical image or fused model that will represent a skin cancer. Cancerous cells having a different density from healthy cells can be rendered in a color corresponding to the particular type of cancer that has been detected. The a hybrid HFU/optical image or fused model can represent the cancer in three dimensions, in a plurality of cross-sectional views and/or in a pseudo-three dimensional representation of a skin volume comprised of two dimensional image slices taken along two separate orthogonal axes.

In some embodiments, the second imaging methodology described herein can comprise biomarker optical imaging (BOI). Various types of BOI imaging methods can be used for this purpose. Biomarkers are well known in the art and therefore will not be described here in detail. However, it should be appreciated that any suitable biomarker can be selected for this purpose provided that it is responsive to the particular type of functional tissue sought to be identified. Likewise, the biomarker can be administered to a patient by any suitable means. For example, the biomarker can be applied topically, injected hypodermically at the site of a suspected cancer, or administered intravenously. With BOI, a biomarker (typically a fluorescent biomarker) is used that emits photons when a certain chemical/biological response or compounds are present. For example, a biomarker could identify high metabolic rate or a specific receptor based on its fluorescent activities or release of photons. An optical imager can be used collect those photons and form an image. The biomarkers used for the purposes of the imaging described herein are advantageously selected so that a cancerous skin lesion will appear to light up or illuminate in captured images so that the cells can be more easily identified when imaged using the second imaging method as described herein.

BOI imaging as described herein can facilitate graphically representing an area in which malignant cells are present. BOI imaging methods and systems are known in the art and therefore will not be described here in detail. However, it will be appreciated that the BOI imaging can be obtained using any type of biomarker and any suitable type of imaging system to capture the image. An RTP workstation for cutaneous oncology ("CO") will accept the BOI images as input.

Other scanning or imaging methods can also be used to facilitate understanding of the anatomy or structural characteristics of the cancer. These methods can be used in place of or in addition to the HFU imaging methods described herein. For example, such methods can include relatively simple laser scanning techniques such as LIDAR (Light Detection and Ranging). Alternatively, more complex scanning methods such as Optical Coherence Tomography (OCT) can be used to obtain detailed structural data associated with the cancer. Unlike LIDAR, it will be appreciated that OCT can penetrate beneath the epidermis. Of course, OCT has some limits with regard to how deep it can penetrate beneath the epidermis, but it can provide a very detailed view of the topology and the anatomy and in some scenarios could be used in place of HFU imaging as described herein. Once a skin cancer has been imaged using the hybrid imaging methods described herein, it can be displayed to a treatment specialist for analysis.

Once visualization of a lesion is provided as described herein, the next step is to facilitate radiation therapy planning to eliminate the cancerous cells. According to a further aspect, this planning process can be facilitated by providing the treatment specialist with a visual understanding of a radiation dose to be applied in combination with the hybrid imaging described herein. In this regard, it will be appreciated that each device used for delivery of radiation therapy to a patient will have a radiation output profile which is determined by various factors, such as the characteristics of radiation filters that are used. This radiation characteristic will generally be unique to each particular radiation therapy device or machine. As an example of the kind of radiation characteristic being described herein, a particular radiation characteristic can define how much of a radiation dose delivered by a particular radiation therapy machine will be delivered to tissue as a function of penetration depth. Such a characteristic is sometimes presented graphically and is referred to as a Percentage Depth Dose ("PDD") plot. As will be appreciated, a radiation output profile such as PDD can be very important to a practitioner who needs to understand how applied radiation from the machine will interact with the tumor at various skin depths.

Consequently, once a skin cancer has been imaged using the hybrid imaging methods described herein, it is advantageous to display the hybrid image (in two-dimensions or three-dimensions) to a treatment specialist together with a superimposed scaled graphical representation of the radiation profile (e.g. a PDD profile) of a radiation therapy device which will actually be used to administer the radiation treatment. In this way, the treatment practitioner can visually evaluate the dose of radiation that will be delivered to various portions of the cancer as displayed, when using a particular radiation delivery device. In some scenarios, the radiation delivery device can comprise an available component of an RTP workstation as described herein. Accordingly, the visual display can align the PDD profile along a vector axis corresponding to an alignment of a radiation therapy beam which is anticipated for use in a particular scenario. The beam alignment or vector direction can be manually input into the RTP, but in many scenarios it can be advantageous to provide a machine for applying radiation therapy in data communication with the RTP such that the RTP can receive information about radiation applicator position and thereafter present the proposed vector direction of applied radiation particles in accordance with a detected position of the radiation applicator.

According to a further aspect relating the treatment planning, a treatment practitioner can create a shield to protect portions of a patient's body from radiation to be applied by a radiation therapy applicator. Such a shield will have a cutout portion which will usually correspond to the shape of a cancer to be treated plus some additional margin around the cancerous tissue. According to a further aspect of the inventive arrangements described herein, an image of the shield including the cutout portion can be acquired and provided to an RTP as described herein. For example, a camera disposed in a radiation applicator unit can capture the image of the shield. The shield image can then be used as described below when visualizing a radiation treatment plan.

In particular, a three-dimensional pattern of radiation can be synthesized or rendered by an RTP workstation whereby the three-dimensional pattern is an irregularly shaped volume determined in accordance with the shield image and vector angle of applied radiation. Consequently, the three-dimensional pattern can visually show where radiation will be applied to underlying tissue as a result of the function of the shield. The irregularly shaped radiation pattern can be superimposed on a previously acquired two-dimensional or three-dimensional hybrid image of the cancerous cell as described herein. The resulting image or three-dimensional model is presented to a treatment specialist on a display device of the RTP so it can be observed. The treatment specialist can then visualize a resulting three-dimensional pattern of radiation which will extend through the skin tissue with the current shield and applicator setup. The shield can then be evaluated to determine whether the cancerous cells at each skin depth are being properly dosed with radiation in accordance with a potential treatment plan.

As will be appreciated, the three-dimensional beam pattern generated by the RTP for visualization purposes will depend in part on a beam alignment or vector direction of a radiation beam applied to the tissue and screened by the shield. Accordingly, the RTP can receive information about radiation applicator position and beam vector direction. Thereafter such information can be used by the RTP to determine and render the pattern and extent of the three-dimensional volume of applied radiation (for visualization purposes). Such pattern can then be displayed in accordance with such vector direction of radiation to be applied, superimposed over the image of the cancer as described herein.

According to a further aspect, the visualization obtained by using the shield can be combined with the graphical display of radiation penetration plot (such as the PDD).

According to a further aspect, the three-dimensional representation of the radiation beam resulting from a particular shield pattern and beam vector can also be automatically evaluated by the RTP machine to determine whether all areas of the cancer are being adequately treated. For example, portions of the cancerous cells that are determined to receive an inadequate dose of radiation can be highlighted in a different color to show the deficiency of the resulting three-dimensional beam patter.

According to a further aspect, the RTP can determine an optimal shield pattern based on a selected vector and the hybrid three-dimensional image of the cancer. The optimal shield pattern, including appropriate margins around the cancerous cells can then be rendered as a two-dimensional pattern. The two dimensional pattern can be output by the RTP in an image format that is suitable to facilitate manually marking and cutting a metal plate which can be used as a shield or template in accordance with a radiation therapy treatment. Alternatively, the RTP can output the shield pattern in a data file format which is suitable for controlling a fabrication machine. In some scenarios, the fabrication machine can be included as part of the RPT workstation. One example fabrication machine that can be used for this purpose can include a tabletop computer numerically controlled (CNC) router (e.g., a CNC machine). However, the embodiments are not limited in this regard and the fabrication machine can also comprise a 3D printer. Thereafter, the fabricated shield or template can be fabricated so that it is available for use in treatment of a patient.

The various aspects disclosed above will be described with respect to the attached drawings of an exemplary system that can deliver both diagnostic and therapeutic functionalities through a single platform and an integrated workflow to better serve and benefit the practitioner and patient with skin cancer and/or skin lesions. The exemplary system provides multiple imaging devices and a radiotherapy device used cooperatively to diagnose, treat and verify treatment in accordance with the present disclosure. Thus, the system can be an image-guided superficial radiotherapy treatment system. The system includes software to analyze and combine data and images produced by the imaging devices to provide pinpoint and focused treatment with the radiotherapy device. Additionally, the diagnostic protocols can be repeated throughout the treatment process to adjust, focus, increase or decrease radiotherapy as appropriate.

The present solution also generally concerns systems and methods for workflow management in a medical context. The methods generally comprise performing at least one of the following operations by a processor (e.g., at least one computer): automatically detecting when a patient arrives at a medical facility using first information acquired from a first mobile device (e.g., a wearable device) coupled to the patient; automatically communicating a notification message indicating the patient's arrival at the medical facility to a communication device coupled to or in proximity to a medical professional; automatically obtaining a treatment plan for the patient from a remote datastore using the first information; and automatically transforming a state of medical equipment from a first configurable operational state to a second configurable operational state in accordance with the treatment plan. The first configurable operational state comprises a state in which radiation of a first dosage is to be applied to a person for a first amount of time. The second configurable operational state comprises a state in which radiation of a second dosage different from the first dosage is to be applied to the person or another person for a second amount of time different from the first amount of time. Other features of the present solution will become evident as the discussion progresses.

Illustrative Medical Equipment Architecture

FIG. 1 illustrates a high level view of an illustrative system 150 in accordance with the present disclosure and its main sub-modules. The illustrative system 150 can include a radiotherapy component 101 with an X-ray tube 100, a solid-state X-ray beam sensing component 102, an ultrasound component 103 with a transducer 104, an Optical Imaging ("OI") component 109 with an associated Image Capture Device ("ICD") 110. The system also includes a system control component 105 for guiding the radiotherapy of the radiotherapy component 101 based on images and data obtained from the ultrasound component 103, transducer 104, OI component 109, and ICD 110. The system control component 105 can also work with the solid-state X-ray beam sensing component 102 to ensure that the radiotherapy is of the appropriate intensity, depth and size. In some scenarios, the system can further include a template or shield fabrication component 111.

The ultrasound component 103 can include control circuitry, system drivers, operation control software, and a transducer 104. The transducer 104 can be a high frequency ultrasonic transducer for superficial epidermis, dermis-level and/or subcutaneous tissue anatomical imaging. The ultrasound component 103 communicates with the software of the system control component 105 via a bus and system drivers. The ultrasound component 103 and transducer 104 are provided in exemplary system 150 to provide structural or anatomical data without exposing a subject to ionizing radiation. However, the present disclosure contemplates that ultrasound component 103 and transducer 104 can be replaced or supplemented in system 150 with components for supporting any other types of imaging techniques that also do not utilize ionizing radiation. These other imaging techniques can include, but are not limited to, optical coherence tomography, Laser range scanning and/or LIght Detection And Ranging ("LIDAR").

The optical imaging component 109 can include control circuitry, system drivers, operation control software, and an image capture device 110 for superficial epidermis, dermis-level and/or subcutaneous tissue functional imaging. According to one aspect, the optical imaging component is a spectroscopic imaging device. For example, the optical imaging component can comprise a multispectral imaging device that captures image data at a plurality of optical frequencies. Such multispectral imaging component can be configured to utilize optical energy from the visible portion of the light spectrum for imaging purposes, but can also utilize optical energy from frequencies beyond the visible light range (e.g., infrared and near ultraviolet). Alternatively, the optical imaging component can comprise a hyperspectral imaging device wherein optical information is captured from across the electromagnetic spectrum at each pixel in the captured image. As a further alternative, the spectroscopic imaging device can be configured for Raman spectroscopy which captures changes in the frequency of photons in monochromatic light which result from interaction with skin tissue.

The optical imaging component 109 communicates with the software of the system control component 105 via a bus and system drivers. The present disclosure contemplates that optical imaging component 109 and the image capture device 110 can be replaced or supplemented in system 150 with components for supporting any other types of imaging techniques for extracting molecular or functional information from tissues. For example, biomarkers can be used to enhance the usefulness of the optical imaging methods described herein. As is known, a biomarker can involve a substance which is introduced to a tissue to facilitate the identification of a disease condition such as cancer. According to one aspect, a biomarker can include any substance introduced to a skin tissue which can be used to induce visually or optically detectable changes that can facilitate identification of cancerous cells. Any biomarker now known or known in the future can be used in conjunction with the optical imaging component 109 and image capture device 110 provided that it can help facilitate identification of functional data pertaining to skin tissue under observation.

The radiotherapy component 101 (which can be a superficial radiotherapy component and X-ray tube 100) can include control circuitry, at least one cooling element for an x-ray tube, power supplies, at least one high voltage generator, at least one interchangeable ALuminum ("Al") filter magazine, at least one collimating applicator, and at least one hardware timer that works in concert with a software timer for redundancy and other purposes.

It is contemplated that the X-ray tube utilized herein will be selected so that it is optimized for superficial cutaneous interaction with skin tissue and has minimal effects at deeper tissue depths. For example, a conventional Superficial Radiation Therapy ("SRT") type of X-ray unit can be used for this purpose. As will be appreciated, an SRT type of X-ray unit produces low energy X-rays that are suitable to treat skin conditions as hereinafter described.

The solid-state X-ray beam sensing component 102 can monitor the beam output of the radiotherapy component 101 and x-ray tube 100, along with overall system stability and yield. The solid-state X-ray beam sensing component 102 is mounted underneath the X-Ray tube 100 and is moved in front of the tube when the system 150 needs to be tested for quality control or overall system 150 diagnosis purposes. Otherwise, it is retracted back in its home position away from the X-ray tube 100 and the X-ray beam in order not to interfere during a normal operating mode.

The present disclosure contemplates that in addition to or as an alternative to using an X-ray based radiotherapy in system 150 any other types of radiotherapy can be used in system 150. Thus, the components for radiotherapy can be selected to support photon-based radiotherapy (e.g., x-rays and gamma rays), particle-based radiotherapy (e.g., electrons, protons, neutrons, carbon ions, alpha particles, and beta particles), or any combinations thereof.

In an exemplary operation, the system 150 utilizes the ultrasound component 103 with a transducer 104 to scan and image a tissue volume of interest, such as a volume of the skin with a lesion, to obtain structural or anatomical information about the region of interest. The system then utilizes the optical imaging component 109 with image capture device 110 to optically scan and image the same volume to obtain functional and/or metabolic information pertaining to the skin tissue or portions thereof. As used herein, the functional and/or metabolic information referenced herein can include any information pertaining to the biological function, behavior or processes at work in a particular cell or group of cells. The ultrasound and optical scanning processes will be described below in further detail. However, it should be understood that each scanning method will advantageously provide image data sufficient in combination to produce a 3D representation of the scanned volume of tissue. In some scenarios, the 3D representation produced by the ultrasound and optical image scanning methods described herein can each individually comprise a plurality of two-dimension image slices taken along one or more orthogonal axes, which can be combined to form a 3D image.

A registration process is used to facilitate alignment of the image data acquired using the ultrasound and optical scanning methods. After the region of interest has been scanned and imaged by the system 150, the image data is processed by the system's software. The image data acquired using the ultrasound and optical scanning methods can be registered and then fused or merged to form a single image. In the fused image, the image data acquired by using ultrasound is basically superimposed over the image data acquired by using the optical scanning method described herein. The result is a hybrid image which includes detailed anatomical and/or structural data for the skin cancer with the functional data for the same tissue volume superimposed.

The system 150 can be used to analyze and quantify the tumor and subsequently prepare a treatment plan that is derived from the actual tumor parameters (e.g., volume, circumference, penetration depth and tissue density). Once the tumor analysis and quantification are complete, the system 150 software provides analytical guidance to deliver the most accurate and appropriate superficial radiotherapy pertaining to the scanned and analyzed tumor. The therapy is then delivered by the integrated superficial radiotherapy component 101. The system's software (a) documents the entire diagnosis and treatment cycle and (b) archives the patient data on a patient data repository 107 and the overall system 150 functionality log on a system data repository 108.

The superficial radiotherapy component 101 can be utilized to treat any tumors, lesions or areas where analysis or diagnosis determines that treatment is needed. The superficial radiotherapy component 101 delivers collimated and focused x-ray photon particles to treatment areas. The treatment can be without any biopsies and the pre-treatment analysis, treatment and post-treatment analysis can be carried out locally without the need for remote sources or analysis. The level of treatment can be determined as set forth below.

The system 150 is controlled and operated by the system control component 105, which can include a central computer with a motherboard that runs operation and control software with various parallel and connected boards that allow it to control, communicate, and monitor the various sub-components and modules of the system 150. This achieves harmonious functionality between the two (2) main clinical components of the system 150. The main clinical components comprise the superficial radiotherapy component 101 and the ultrasound component 103. The superficial radiotherapy component 101 provides radiotherapy treatment. The ultrasound component 103 is utilized to scan and acquire the anatomy and topology of a patient's skin area of concern for further analysis, diagnosis, quantification, and therapy planning purposes. The system control component 105 can be connected with data repositories, including a patient data repository 107 and a system data repository 108. The system 150 can also be connected to a network 106 (e.g., a local area network, a wide area network and/or the Internet), which allows for clinical and system data exchange with remote systems or networks.

The system control component 105 can be configured to output a 2D pattern for a template or shield to be used during radiation treatment for masking or shielding certain portions of a patient's skin. The 2D pattern can be output to a user in the form of an image or pattern that is suitable to facilitate manually marking and cutting a metal plate which can be used as a shield or template in accordance with a radiation therapy treatment. Alternatively, the control component 105 can output the shield pattern in a data file format which is suitable for controlling a fabrication machine. In some scenarios, a fabrication machine 111 can be included as part of the system 150. One example of a fabrication machine 105 that can be used for this purpose can include a tabletop Computer Numerically Controlled ("CNC") router (e.g., a CNC machine). However, the invention is not limited in this regard and the fabrication machine 111 can also comprise a 3D printer that is capable of 3D metal printing. Thereafter, the fabricated shield or template can be fabricated by the fabrication machine 111 so that it is available for use in treatment of a patient.

The patient data repository 107 and the system data repository 108 can be a solid-state drive, hard drive or other memory device. The patient data repository 107 can store patient-related data and treatment parameters, such as patient records, treatment session chronology, and disease documentation and photos. The system data repository 108 stores all system-related data and parameters, such as the system log, x-ray calibration data, and system diagnostics results. The patient data repository 107 and the system data repository 108 can be discrete devices or physically combined. One or more partitions can be used if the repositories 107 and 108 are combined, such as a single repository.

Figure 2:
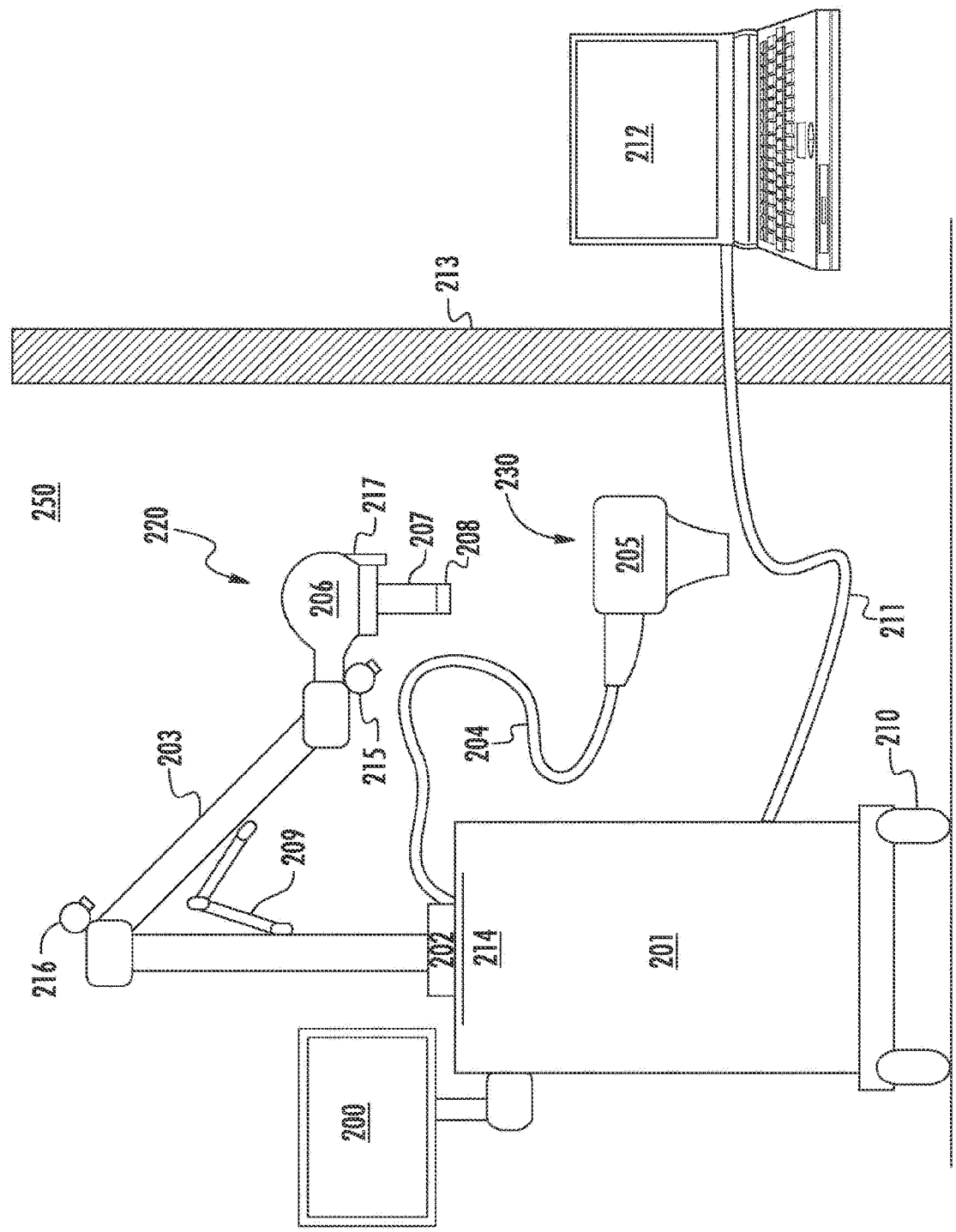
FIG. 2 is an illustration of an illustrative image-guided radiotherapy system.

In some scenarios, an ultrasound guided radio therapy treatment and diagnostic system 250 is shown in FIG. 2. The system 250 can include a base unit 201 with various components mounted thereon or connected therewith. These components can include a radiotherapy treatment device 220 and its various components and an imaging subsystem 230.

The base unit 201 can be typically a compact unit such as one with a 30"×30" footprint and can be mounted on casters 210 for ease of maneuverability. The base unit 201 can include a power lead for optionally providing power to all of the components housed in or connected to the base unit 201. In this regard, the base unit 201 can contain one or more computers for controlling the system 250 components and/or analyzing and processing data obtained from the system 250 components. A monitor 200 can also mounted to the base unit 201 for a user interface. Likewise, a terminal or an input device 214 (e.g., a keyboard or a mouse) can be included.

A mount 202 is provided on the base unit 201 for mounting the radiotherapy treatment device 220. The radiotherapy treatment device 220 can include a treatment arm 203 and treatment head 206, which can include removable or movable applicators 207, 208. The treatment arm 203 is articulated with appropriate retractable articulations 209. Although not shown in FIG. 2, additional articulations can also be provided at different points of system 250 to increase a number of degrees of freedom of placing and orienting treatment head 206. For example, additional articulations can be provided between treatment arm 203 and treatment head 206 and between mount 202 and treatment arm 203. Moreover, the number of articulation points illustrated in FIG. 2 is solely for ease of illustration. The present disclosure contemplates that the any number of articulation points between mount 202 and treatment head 206 can be provided so as to provide any number of degrees of freedom in treatment arm 203 required positioning and orienting the treatment head with respect to the patient.

A camera 216 can also be included to provide for remote operation or for documentation of treatment. A video-laser positioning system having camera 215 and laser or light pointer 217, which visibly marks a region with a crosshair that will receive radiotherapy treatment, can be provided. The camera 215 can capture low opacity images of the radiotherapy treatment head 206 and crosshairs of laser pointer 217 during treatment so that the exact positioning and orientation can be reproduced during subsequent treatments. In this regard, the video-laser positioning system can identify proper and precise positioning and orientation of treatment head 206. The video-laser positioning system can also allow for remote control and operation of the treatment arm 203 so that the treatment head 206 can be positioned precisely while the user is remote. In operation discussed below, the treatment arm 203 can be articulated and positioned to allow the treatment head to apply radiotherapy to a patient.

The imaging subsystem 230 can include at least one imaging head 205 attached via a corresponding lead 204 to the base unit 201 and data acquisition and processing machinery housed therein. The imaging head 205 can be a compact hand-held unit tethered to the base unit 201 by the corresponding lead 204. As such, the imaging head 205 can be freely moved to facilitate scanning different skin locations on the body of a patient. In operation, the imaging subsystem 230 can be used to collect both images and data of a diagnosis or treatment area before, during or throughout and after treatment. In some arrangements, an imaging head 205 can be mounted on the arm 203 instead of being provided separately.

Each imaging head can include components needed for supporting an imaging modality. For example, referring back to FIG. 1, a first imaging head 205 can be provided that includes ultrasound component 103 and transducer 104 and a second imaging head 205 can be provided that includes optical imaging component 109 and image capture device 110. However, the present disclosure also contemplates combined functionality. That is, a single imaging head 205 can incorporate ultrasound component 103, transducer 104, optical imaging component 109, and image capture device 110.

Lead 211 can connect the system 250 to another computer 212 or use interface that can be positioned behind a shield 213 for remote operation of the system 250 or components of system 250, such as the radiotherapy treatment device 220.

Figure 3:
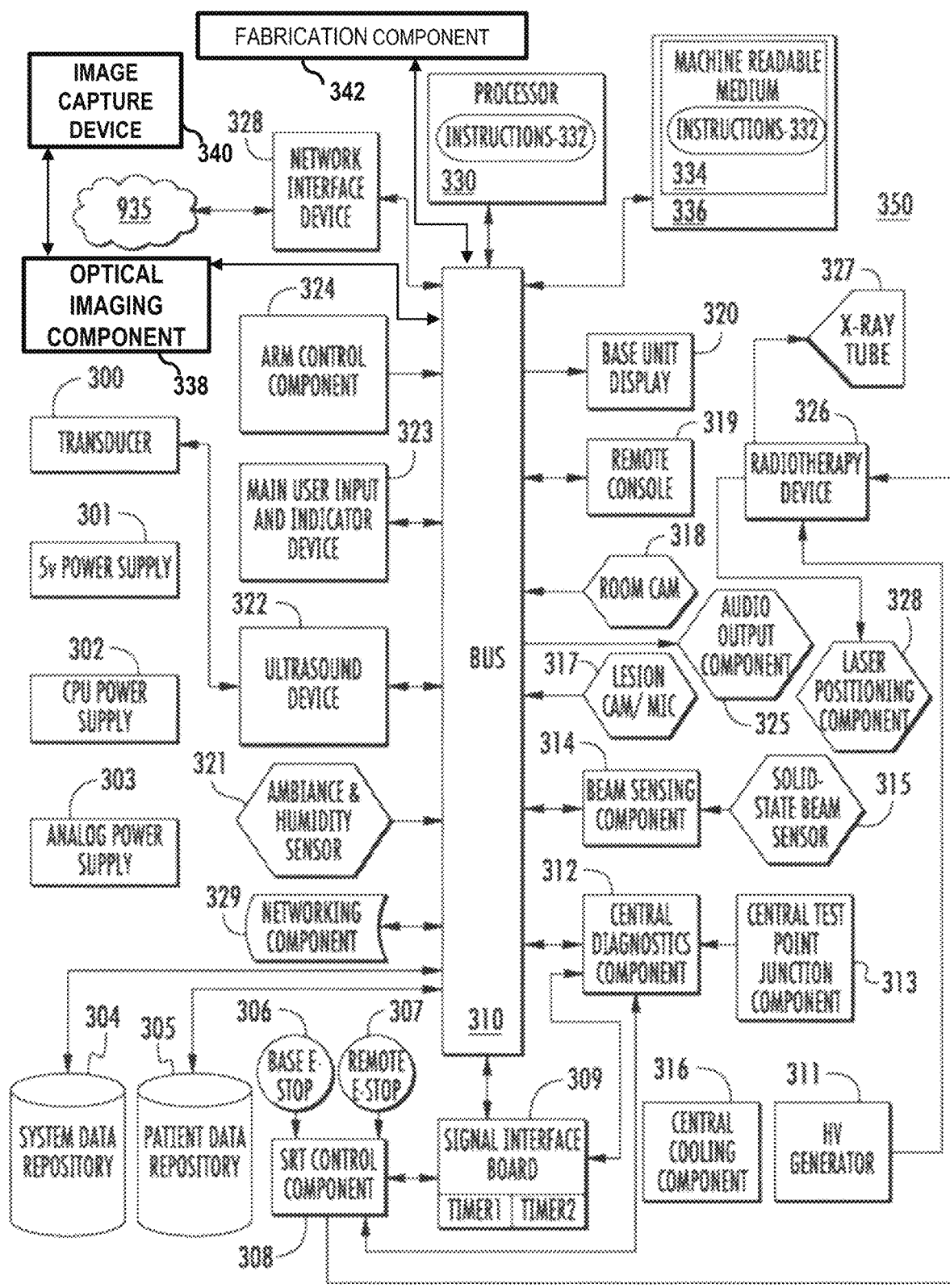
FIG. 3 is an illustration of another illustrative image-guided radiotherapy system.

FIG. 3 illustrates a schematic view of various components and sub-components of RTP system 350. The system 350 can include a bus 310 through which the various components can communicate with each other and/or the processor 330 (e.g., a Central Processing Unit ("CPU"), a Graphics Processing Unit ("GPU"), or both). The processor 330 can be connected to the bus 310 as shown in FIG. 3 or integrated therewith. Power supplies 301, 302, 303 can also be included.

The system 350 can be controlled and operated by processor 330 that runs the system 350 software or instructions 332, which controls the system 350 functions, verifies the safety mechanisms, and the service and calibration functions. The processor 330 can be in communication with a machine-readable medium 334 (e.g., a static memory 336) on which is stored one or more sets of instructions 332 (e.g., software) embodying any one or more of the methodologies or functions described herein, including those methods illustrated herein. The instructions 332 may also reside, completely or at least partially, within the system data repository 304, static memory, within the processor 330, or a combination thereof during execution thereof by the system 350. The system data repository and patient data repository and the processor 330 also may constitute machine-readable media.

The processor 330 can be in communication with a motherboard having an appropriate amount of static or dynamic RAM, such as 4 GB of DRAM, in order to optimally support and accommodate the operating system, main software, and real-time system monitoring functions, together with efficient patient and data system handling and archiving. The system 350 software also communicates with the peripheral components, such as Ethernet, USB, and audio/video or via network interface card 338 in order to implement the system's user/machine interface and exchange data with external workstations and data repositories (e.g., such as Electronic Medical Records ("EMR"), Electronic Health Care Records ("EHCR"), Hospital Information Systems ("HISs"), Radiology Information System ("RIS"), and Picture Archiving and Communication Systems ("PACS")) utilizing Digital Imaging and Communications in Medicine ("DICOM") and Health Level 7 ("HL7") communications and data structure protocols.

The system 350 can include storage mediums 304 and 305, such as solid state drives, hard drives or the like. Storage medium 304 can be the system data repository, which can include the operating system, the main system software, and system data and parameters archive. Storage medium 305 can be the patient data repository 305, which stores all patient-related data and records.

The system 350 can include a base unit that houses or otherwise provides various components of the system 350, including user interfaces. The base unit can include a base unit display device 320 (e.g., an LCD display and a base unit user input) and indicator device 323 (e.g., a terminal or a mouse). The system 350 can also include a remote console 319 that can be used to remotely control the system 350 so that a user does not need to be present during radiotherapy treatment. The base unit user input and indicator device 323 allows the user to interact with the system 350. The base unit user input and indicator device 323 can be utilized for initial patient data setup on the system 350 and for the ultrasound imaging of the patient's tumor at various stages of the disease before, during, and after the superficial radiotherapy period. Furthermore, the base unit user input and indicator device 323 can also be a terminal of the system 350 software. The diagnostics results and images, patient data, remote workstations topology, patient and room monitoring data, system service menus, system physics and calibration menus, and all system queues and alerts can be displayed on the base unit display device 320 or via the base unit user input and indicator device 323 as appropriate.

The system 350 can also include an ultrasound device 322 with a transducer 300. The ultrasound device can obtain structural or anatomic images of the treatment area or skin lesion of concern. With the ultrasound device 322 with a transducer 300, diagnostics of the area of concern can be processed. The ultrasound device 322 can be any ultrasound device capable of operating within an acceptable bandwidth. For example, the high frequency ultrasound device 322 can operate in a bandwidth of approximately twenty Mega Hertz (20 MHz) to approximately seventy Mega Hertz (70 MHz), and may be implemented with an electro-mechanical, or solid state transducer. The system 350 can provide the ultrasound imaging device 322 at least partially integrated inside a system 350 housing coupled to bus 310 with a transducer head outside of the housing as shown in FIG. 2. The ultrasound device 322, and other components of the system 350, can be in communication with the bus 310 and the respective other components of the system 350 utilizing interface standards such as Peripheral Component Interconnect ("PCI" or "PCIe"), Universal Serial Bus ("USB", "USBII" or "USBIII"), or Firewire. However, the present disclosure contemplates that any other interface and/or communications standards can be used.

The system 350 can also include an optical imaging component 338 with an optical image capture device 340. As explained above, an optical imaging component 338 can obtain functional images of a 3D volume comprising a treatment area or skin lesion of concern. With the optical imaging component 338 and image capture device 340, image data representative of the treatment volume of concern can be obtained and processed.

The optical imaging component 338 can include any type of image capture device now known or known in the future. According to one aspect, the optical imaging component can comprise an electronic image capture device 340 that captures incoming photonic radiation and converts same into electrical signals. An image capture device of this type can be comprised of a focusing element (e.g. a lens), a charge-coupled device (CCD) or a CMOS image sensor, and readout circuitry for acquiring the image data. Image capture devices as described herein are well known and therefore will not be described here in detail.

The system 350 can provide the optical imaging component 338 at least partially integrated inside a housing of system 250 coupled to bus 310 with an image capture device 340, outside of the housing as shown in FIG. 2. The optical image component 338 and other components of the system 350 can be in communication with the bus 310 and the respective other components of the system 350 utilizing interface standards (e.g., PCI, PCIe, USB, USBII, USBIII, and/or Firewire). However, the present disclosure contemplates that any other interface and/or communications standards can be used.

The system 350 can further include a radiotherapy device 326 that includes an SRT X-ray tube 327. As discussed herein, the radiotherapy device 326 that includes an X-ray tube 327 can deliver pinpoint radiation therapy to a particular region or area on a patient. The radiotherapy device 326 can be coupled with a high voltage generator 311 and a central cooling component 316.

The system 350 can also include a control component (e.g., a superficial radiotherapy control component 308) for controlling the radiotherapy provided by radiotherapy device 326. The superficial radiotherapy control component 308 can control aspects of the radiation dosage, including timing, depth and intensity. In this regard, an arm control component 324 can also be provided with the system 350 and in communication with the superficial radiotherapy control component 308 and/or processor 330. The arm control component 324 can move, articulate or otherwise control positioning of the arm to which the radiotherapy device 326 and x-ray tube 327 are mounted. A base e-stop 306 and remote e-stop 307 can also be provided to provide local and remote emergency termination functions so that the radiotherapy device 326 can be stopped either locally or remotely.

Additionally, solid state beam sensing component 314 with a solid-state beam sensor 315 can be provided. In some scenarios, these components can be housed within the housing of X-ray tube 327. The solid state beam sensing component 314 with a solid-state beam sensor 315 provide the ability to obtain on demand and local analysis of the radiotherapy device 326 with X-ray tube 327. Utilizing the solid state beam sensing component 314 with a solid-state beam sensor 315, the radiotherapy device 326 with X-ray tube 327 can be tested to determine if the radiation output is consistent with the desired radiation output. In the event that there are discrepancies, the devices can be re-calibrated or otherwise serviced.

A central diagnostics component 312 can also be provided and can be interfaced with bus 310 and processor 330. The central diagnostic component 312 is also connected with a central test point junction conjunction 313 and additionally interfaces with a signal interface board 309 that is in turn connected to both the processor 330 through bus 310 and the superficial radiotherapy control component 308. The signal interface board 309 can also include a first and second timer for redundant time counting during the application of radiation therapy, which provides for added patient safety and accurate dosimetry calculation for the delivered therapy dose to the patient. In addition to the dual hardware timers, one or more additional software based timers can be utilized or invoked by system 350.

The central diagnostics module 312 is a systems diagnostic component that monitors the various system boards and components for failures and/or errors. The central diagnostics module 312 can generate alerts regarding the system status that can either be communicated with the user, or with the system installer or manufacturer for maintenance purposes.

Additional inputs can be connected to the processor 330 through bus 310 including a camera and/or microphone 317, an audio output component 325, such as a speaker, a room camera 318 for taking pictures or video of the patient, treatment areas and/or the treatment process. An ambiance and humidity sensor 321 can also be provided in the event that conditions may affect the treatment or any of the system 350 components. However, the arrangement is not limited in this regard. A fabrication component 342 for fabrication of a metal shield or template can also be connected to the bus 310 in some scenarios.

Figure 4A:
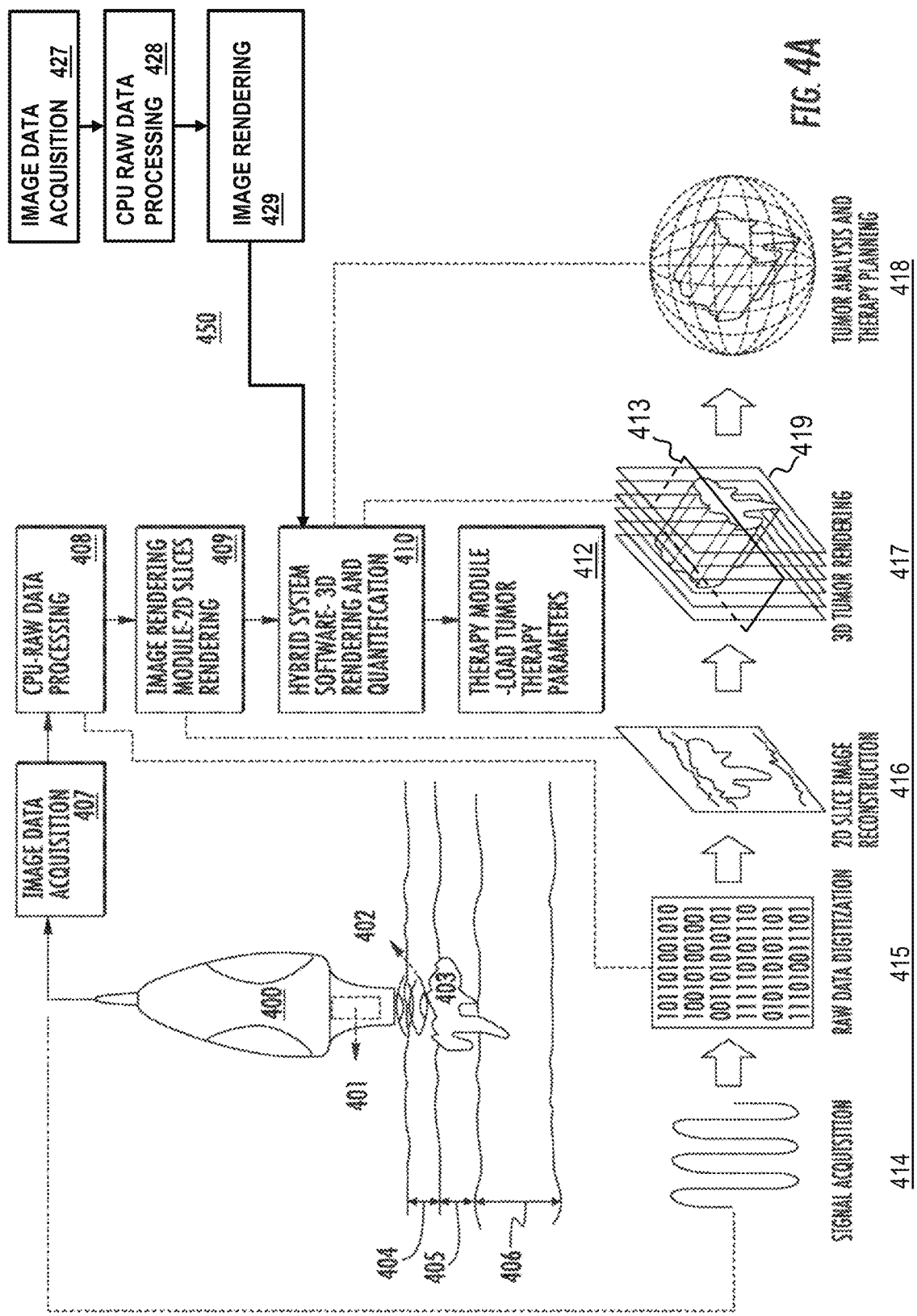
FIG. 4A is a flow diagram of a tumor imaging and quantification process.

FIG. 4A illustrates an exemplary process 450 with at least one imaging device 400, along with subsequent a tumor processing, rendering and analysis method and process 450. As an example, the method and process 450 can be used with systems 150, 250 and 350, and their software that can be integrated with or operatively in communication with various system components as shown in FIGS. 1-3.

As shown in FIG. 4A, an ultrasound head or device 400 includes an ultrasound transducer 401 located in the head 400. High frequency ultrasound is used for the imaging, which provides a much clearer image in comparison to low frequency ultrasound, but which does not penetrate deeply into the skin. High frequency ultrasound can include frequency ranges of approximately twenty Mega Hertz (20 MHz) to approximately seventy Mega Hertz (70 MHz), such as approximately thirty-five Mega Hertz (35 MHz) to approximately fifty-five Mega Hertz (55 MHz).

In operation, the method and process 450 can begin with obtaining ultrasound image data. Using imaging device 400, an ultrasound beam 402 is aimed at an area of concern (e.g., lesion 403) through the epidermis 404, dermis 405 and subcutaneous fat 406. In use, the transducer 401 sends high frequency ultrasonic waves towards the epidermis 404, dermis 405 and subcutaneous tissue 406 where the tumor 403 is located in varying depth, circumference, and volume. The reflected ultrasonic waves 402 that hold the tumor's physical characteristic data (structural/anatomical data) are acquired by the transducer 401. For example, the structural/anatomical data collected can include a density characteristic of the tissue which is being imaged. A lesion will have a density that is different from surrounding healthy tissue and can therefore be easily differentiated within the captured image data. The difference in density can allow the location and boundaries of the lesion to be determined. As an example, a non-melanoma skin cancer lesion 403 is located as shown, and the lesion 403 may extend away from the epidermis 404 and into the subcutaneous fat 406.

Data and images 419 obtained by the ultrasound device 400 are acquired by an image data acquisition component at step 407 and pre-processed for further processing, as shown with the flow diagram of FIG. 4A. The image data acquisition 407 can be followed by processing at CPU at step 408, in which the CPU processes the raw data captured by the image data acquisition at step 407. Thereafter, at step 409, the central processing unit can execute instructions of software to process the data to create and render 2D images, which are acquired in slices across the area imaged by the ultrasound device 400. As an aid to understanding, operations 407, 408 and 409 are graphically illustrated at 414, 415 and 416.

The data and images obtained by the ultrasound device comprise structural data that is useful for representing the skin cancer lesion 403. At 427-429, functional data is also obtained for the skin cancer lesion 403. The functional data can be acquired using an optical imaging component as described herein. Such optical imaging component can comprise a separate image capture head or can be incorporated into the imaging device 400 so that both types of image data can be captured concurrently. Accordingly, the acquisition of functional data can begin at 427 with the acquisition of raw image data. The process can continue to 428 where the central processing unit can execute instructions in software to process the data so as to create or render a 2D image at 429.

Steps 427-429 can involve performing optical imaging using a spectroscopic imaging device to obtain a two-dimensional optical image 413. For example, the optical image can be obtained by using a technique such as multi-spectral imaging, hyperspectral imaging and/or Raman spectroscopy to capture and generate two-dimensional biological or functional image data for the tumor.

The process continues at step 410, which involves fusing the structural data obtained in steps 407-409 and comprising the 3D model, with functional data 413 obtained in steps 427-429. This steps is graphically shown in 417, which shows that the optical image 413 obtained in steps 427-429 can be a 2D image which corresponds to an image plane that is essentially orthogonal to the 2D image slices 419 comprising structural data obtained using high-frequency ultrasound. The image plane corresponding to the optical image 413 will generally correspond to the outer surface of the skin tissue. The nature of a particular skin lesion will be consistent throughout the lesion, so it is not necessary to capture the functional data associated with the cells at all skin depths.

According to one aspect, registration/location information associated with the optical imaging in step 427 and the image acquisition in step 407 can be utilized to fuse the optical image data with the 3D model. Thereafter, the model can be updated or enhanced to indicate both structural and functional information regarding the tumor. Methods for image registration are well known in the art and therefore will not be described in detail. However, it will be appreciated that the two images can be registered by using techniques involving fiducials or pattern recognition methods.

Once the images are registered, the information they contain can be combined into the fused 3D model. This can be done in a variety of ways. In some configurations, the structural image data can be provided in grayscale and the functional image data can be provided as a color overlay to indicate the functional information. In another configuration, the structural image data can be provided in grayscale or color and the functional information can be used to adjust the data in the structural image data. For example, the function information can be used to attenuate one or more color properties of data in the structural image data.

As noted above, the UHF imaging can differentiate such cells as having a density different from adjacent healthy/ normal skin cells. Accordingly, in a subsequent data fusion process, the cells having a first density associated with a cancerous lesion can be highlighted, marked or otherwise displayed in a certain way to differentiate them from the adjacent healthy skin cells. For example, the cancerous skin cells can be displayed in a different color as compared to normal skin cells.

Once biological/functional nature of the tissue comprising the lesion has been determined using the optical imaging methodology, all of the cells which are identified as being associated with the lesion can be marked accordingly. Therefore, the image combining step can involve evaluating each voxel associated with the 3D model which was generated using ultrasound to determine whether a tissue density at particular voxel location differs from a density of healthy tissue at surrounding locations. If a particular voxel density at any skin depth corresponds to the lesion (e.g., cancerous tissue), then the voxel can be assigned a voxel color value associated with cancerous tissue. The voxel color can determine the color that the voxel is displayed as when rendered. But if a particular voxel density at any skin depth corresponds to healthy tissue, then it can be assigned a different voxel color value. Accordingly, the functional or biological information captured using a 2D optical imaging technique can be extended or used to assign a color values to all of the voxels in the 3D model obtained by using ultrasound methodology. The result is a hybrid or fused 3D model containing information from both ultrasound and optical imaging methodologies.

Thereafter, when the fused 3D model is rendered, the cancerous skin tissue can appear as a different color as compared to the surrounding healthy skin tissue. The particular color chosen for the cancerous tissue can be determined by the type of cancer. For example, tissue identified as a BCC can be assigned the color yellow, tissue identified as an SCC can be assigned blue, and tissue comprising a melanoma can be assigned the color red. Accordingly, when the fused 3D model is rendered to a treatment specialist, the boundaries and type of lesion can be easily apprehended.

In some configurations, the resulting fused 3D model may not provide a "real world" representation of the tumor. That is, the color and other properties of the fused 3D model may not correlate with what a physician or diagnostician is accustomed to reviewing in a microscope slide or other specimen during a biopsy. Accordingly, the present disclosure contemplates that in some configurations, to ease review and treatment planning, an additional translation or transformation may be used. That is, a transformation matrix can be provided for converting the raw fused 3D model into a 3D model that visually corresponds to what a physician or diagnostician is accustomed to reviewing in a microscope slide or other specimen during a biopsy.

The fused 3D tumor model can be passed to the therapy module at 412, which can be hardware or software, for tumor analysis and therapy planning. The therapy module can be used to analyze the 3D tumor, structurally and functionally, and calculate the designated treatment area voxel, along with the pertinent dosimetry to be applied by a radiotherapy device. The dosimetry can include measurements and calculations of the absorbed dose in tissue resulting from the exposure to radiation. In one example, the appropriate treatment volume can be a spherical shape or a cylindrical shape. Alternatively, the appropriate treatment volume can be any other suitable shape that will leave appropriate treatment margins around the tumor. The accuracy provided by the hybrid imaging allows the treatment margins to be of the order of ten percent (10%), which is a significant improvement over the typical three hundred percent (300%) treatment margins used in Mohs surgery.

Additionally at step 412, appropriate therapy can be determined using the fused 3D model from step 410. The therapy software can include vector tables identifying the appropriate radiotherapy dosages for different sized tumors. This allows the system to precisely calculate therapy parameters, including treatment dosage based on the actual size of the tumor, including its depth and volume, rather than relying on the physician having to estimate the tumor size and depth based on experience and the visible surface area of the tumor.

From the foregoing discussion, it will be understood that a hybrid or fused 3D tumor model or volumetric model can be rendered. A 3D construction and rendering engine can combine all or a portion of extracted 2D tumor slices obtained using ultrasound and optical imaging methods as described herein. The data from each scanning process can be merged and the system will fuse them into an integrated 3D model that represents and manifests the tumor's 3D anatomical and functional features. During the construction and rendering sequence, the 3D engine can apply geometrical corrections, smoothing and anatomical triangulation to the rendered 3D tumor model in order to achieve a correlation with the actual scanned or imaged tumor.

Figure 4B:
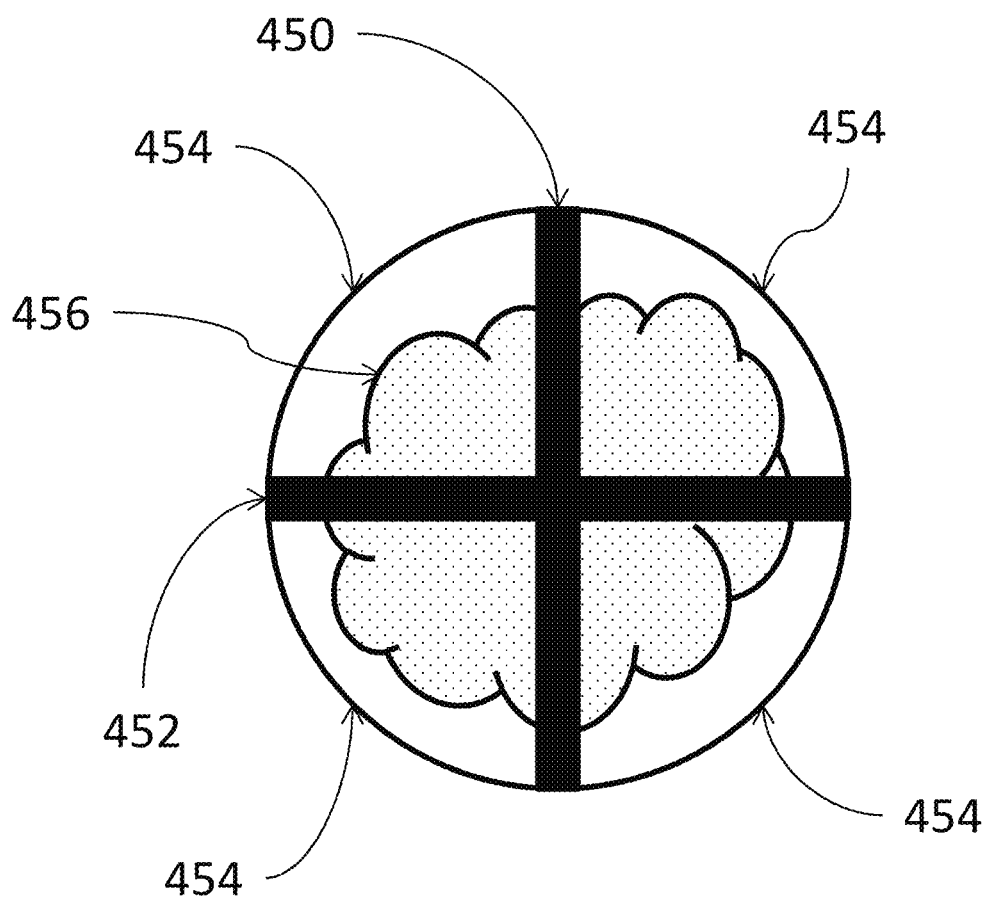
FIG. 4B illustrates an illustrative method for generating a 3D model of a tumor.

However, in some configurations, it may not be desirable to acquire a large number of slices to generate the 3D tumor model. In particular, the 3D tumor model can be generated from two 2D slices, as shown in FIG. 4B. That is, a first slice 450 and a second slice 452, perpendicular to each other, can be selected. Thereafter, the volume in the areas between the slices 454 can be extrapolated from the data associated with the first slice 450 and the second slice 452 and an estimated 3D model of the tumor 456 can be generated. In some configurations, the edges of the tumor in the first slice 450 and the second slice 452 can be identified and the estimated 3D model of the tumor 456 can be generated from only the data in the first slice 450 and the second slice 454 associated with the tumor in these slices.

The process illustrated in FIG. 4B expedites the 3D modeling process as only limited 2D data is required to generate the estimated 3D model of the tumor. In some scenarios, treatment planning does not require a highly accurate 3D model of the tumor, in which case the estimated 3D model of the tumor 456 will suffice. However, the present disclosure contemplates that in other configurations that a similar process can be performed using any number of 2D slices. In either scenario, the physical image data and functional image data will be fused as described herein with respect to FIG. 4.

Figure 5:
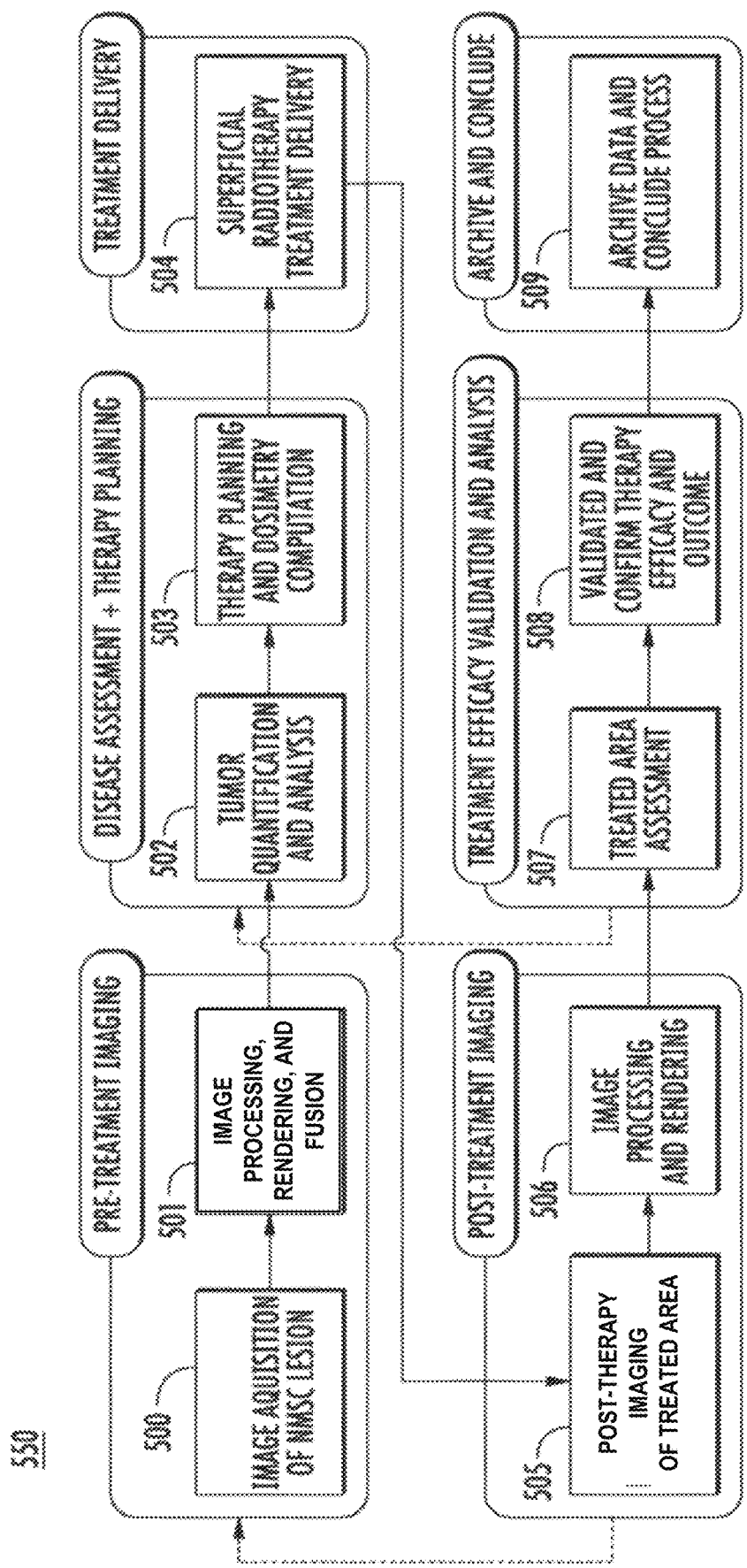
FIG. 5 is flow diagram of a method of diagnosis and treatment.

Referring now to FIG. 5, there is provided a flow diagram of an exemplary method 550 of diagnosis, therapy planning, radiotherapy treatment, post treatment diagnosis and treatment validation and analysis. Although the flow diagram illustrates the steps as sequential, the steps can be completed in different logical orders and some steps, or groups of steps, can be repeated as needed.

The method 550 can begin during a pre-treatment imaging stage at step 500 with image acquisition of an area of concern, such as a non-Melanoma Skin Cancer ("NMSC") lesion or a tumor. This is utilized to acquire the structural and functional parameters of the lesion or tumor. Acquired data and images are then transferred to the image processing, rendering, and fusion step 501. As noted above in reference to FIG. 4A and the corresponding discussion, image data regarding structural features is subject to image processing and rendering and combined with image data regarding functional or molecular features at step 501 to generate a 3D model of the tumor and, optionally, of surrounding tissues.

The method then moves on to a disease assessment and therapy planning stage starting at step 502. At step 502, the lesion or tumor in the 3D model is assessed, defined, quantified, and diagnosed. This can include any classifications for skin cancer type. The assessment at step 502 is based on both the structural and functional features of the 3D model. The 3D model provides a user, such as doctor or clinician, with a local means to diagnose the skin cancer type instead of using the time consuming and invasive biopsy method. However, the present disclosure contemplates that automated diagnosis systems can be utilized, with or without a user confirmation step. Such automated diagnosis systems can utilize, for example, pattern recognition techniques to identifying one or more portions of the 3D exhibiting signs of disease.

Based upon the initial imaging and analysis data, including any classification as to a type of skin cancer, the clinician and patient can decide to proceed with superficial radiotherapy to treat the diagnosed skin cancer lesion. Thus, during the disease assessment and therapy planning stage, tumor quantification and analysis can also occur at step 502 to identify a suitable treatment volume for the tumor that provides acceptable margins. Based on the 3D model and the treatment volume, a tumor volumetric model is provided.

With the tumor volumetric model, therapy planning and dosimetry computation can occur at step 503. Therapy planning and dosimetry computation is carried out at step 503 where the data and images passed from step 502 can be further manipulated and analyzed, including analysis of the tumor and therapy factors. The therapy planning can include not only the dosimetry computation, but also planning for the best location on the skin to reach the center of the tumor and the best angle of presentation for the treatment head. To plan treatment, the 3D tumor model can be orientated in correlation to the anatomy of the area to be treated. Physiological, topographic, and radiation therapy dosimetry parameters can be applied to compute and design the treatment plan, beam targeting and guidance, including the treated area voxel. A fractionation scheme and treatment head positioning on the patient can also be determined. The treatment plan can then completed and loaded into a patient record and scheduler.

In some configurations, the treatment planning can involve generation of a mask or shield formed of a thin plate of material such lead. An exemplary mask or shield as described herein can be understood with reference to FIG. 6 an X-ray tube housing 611, such as the X-ray tube in treatment head 206 of FIG. 2. The X-ray component or device 650 can include a Bremsstrahlung beam-hardening aluminum filter 607 to control the x-ray beam 612 output from the x-ray tube 600. As shown, an X-ray beam aligned along a vector direction 658 can be applied by an applicator unit 609, which limits the overall cross-section of the beam. In order to limit the amount of irradiated tissues, the mask 652 can be generated. The mask can be placed over the patient's body, where the mask includes an aperture or cutout portion 654. The cutout portion is sized and shapes to allow radiotherapy to be applied to a more limited area of the patient's body. The aperture or cutout area 654 is advantageously cut to the shape of the cancerous lesion but includes a further margin which extends a predetermined distance beyond the outer periphery of the cancerous cells. Only that portion of the X-ray beam that passes through the cutout will interact with the cancerous cells. Moreover, since the mask acts as a shield to radiation, high doses can be applied to the cancerous cells or lesion, since concerns with irradiating healthy tissues are significantly reduced.

According to one aspect of the invention, the aperture or cutout area 654 of the shield 652 can be designed based on the 3D hybrid image of the cancerous cells comprising the tumor. An RTP system (e.g., processor 330 associated with RTP system 350) can determine an optimal shield pattern based on a selected beam vector and the hybrid image of the cancer, which has been generated using the techniques described herein. Thereafter, the RTP system can provide a scaled shield pattern as a data output (e.g., output using a network interface device 328) to facilitate fabrication of an optimal shield for use in treatment. The shield can then be manufactured manually or by suitable automated means. For example, the data output data from the RTP system can be in a format suitable for a conventional Computer Numerical Control ("CNC") type machine which uses a computer to control machine tools. Alternatively, the data output can be communicated to a 3D metal printer capable of printing 3D metal parts. Consequently, the shield can be manufactured automatically and with high precision. In some configurations, where the treatment planning calls for radiotherapy to be provided at various angles, a different mask 652 can be provided for different angles or groups thereof, where the shape of the aperture 654 can be adjusted based on the 3D model and the radiotherapy angle to be used.

According to a further aspect, an image of the mask or shield 652 (including the aperture or cutout portion 654) can be acquired by an imaging device. The image can then be provided to an RTP as described herein. For example, an imaging device 656 disposed in a radiation applicator unit 609 can capture the image of the shield 652, including the aperture or cutout 654. The shield image can then be used as described below when visualizing a radiation treatment plan.

Figure 9:
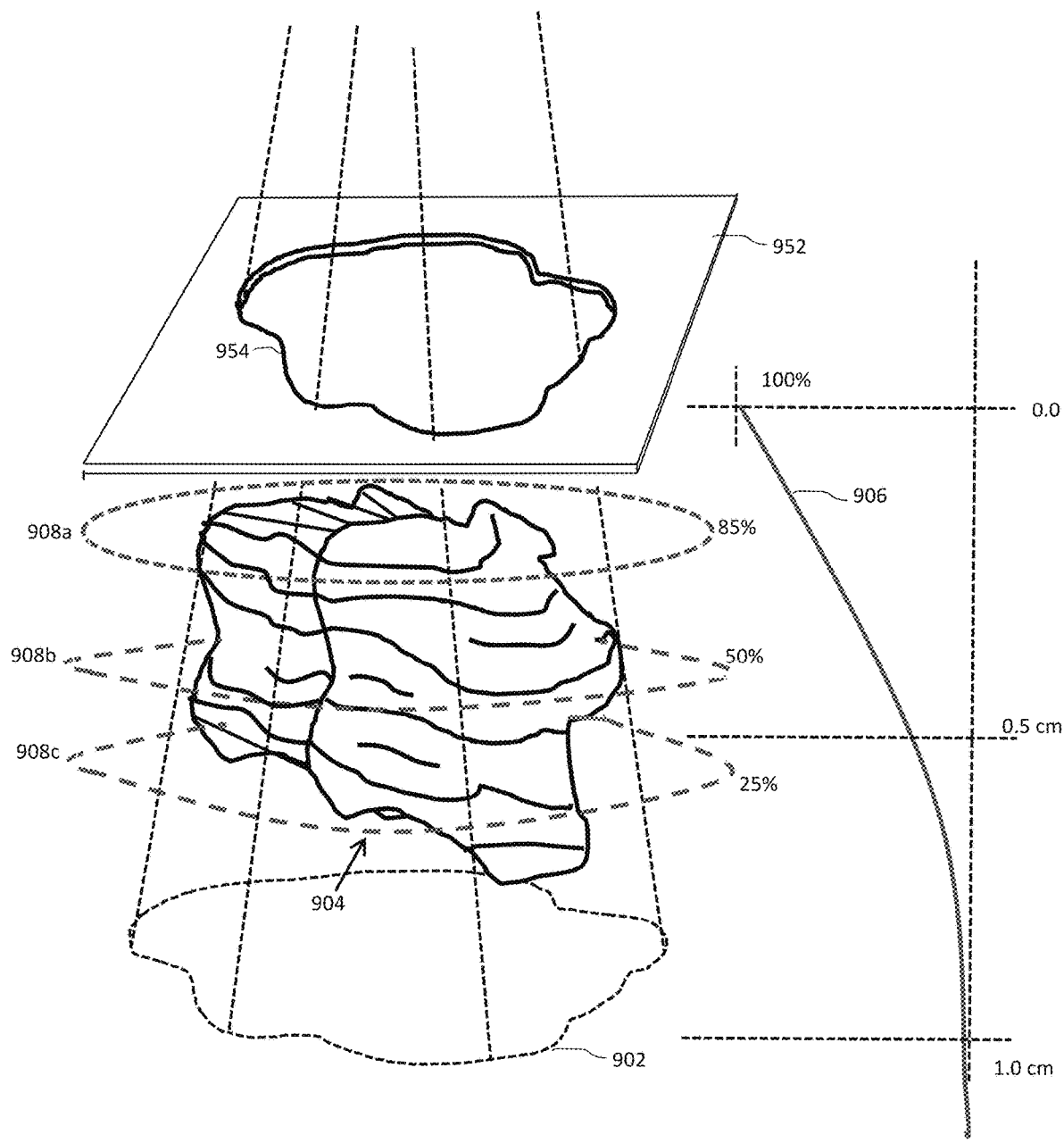
FIG. 9 is a diagram that is useful for understanding a beam projection created by using mask or shield.

Referring now to FIG. 9, a 3D pattern 902 of radiation can be synthesized or modeled by a processor in an RTP system (e.g., processor 330 in RTP system 350) whereby the 3D pattern is an irregularly shaped volume is determined in accordance with the captured shield image 952 and vector angle of applied radiation. Consequently, the 3D pattern can visually show where radiation will be applied to underlying tissue as a result of the function of the shield and the imaged aperture 954. The irregularly shaped radiation pattern can be superimposed on a previously acquired 2D or 3D hybrid image of the cancerous cells 904 as described herein. The resulting composite image as shown in FIG. 9 is then presented to a treatment specialist on a display device (e.g., on base unit display device 320) of the RTP so it can be observed. The treatment specialist can then use the displayed image to visualize a resulting 3D pattern of radiation which will extend through the skin tissue when using the shield 652 and applicator unit 609. The shield can then be evaluated to determine whether the resulting 3D beam representation is intersecting all of the desired cancerous cells at each skin depth. Accordingly, the treatment specialist can determine whether the cancerous cells are being properly dosed with radiation in accordance with a potential treatment plan.

From the foregoing, it will be understood that the 3D pattern 902 generated by the RTP system for visualization purposes will depend in part on a beam alignment or vector direction 658 of a radiation beam applied to the tissue and screened by the shield 652. A processor associated with the RTP system (e.g., processor 330 associated with RTP system 350) can receive information about the shield aperture 654 and the radiation applicator 609 (including position and beam vector direction). Thereafter, such information can be used by the RTP processor to model the beam pattern as shown in FIG. 9 and to show the extent of the 3D volume of applied radiation (for visualization purposes). Such pattern can then be displayed (e.g., on a base unit display 320 or on a remote console 319) in two-dimensions or three-dimensions. Advantageously, the displayed 3D image comprising the modeled radiation beam 902 can be superimposed over the hybrid image of the cancerous tissues 904 so a treatment specialist can visually evaluate whether the beam will be applied to all portions of the tissue that are determined to be cancerous.

According to a further aspect, the visualization in FIG. 9 that is obtained by using the shield 652 and vector 658 data can be combined with a further graphical display of certain data. For example, such graphical display of data can be data that is useful for understanding a radiation dose which will be applied at various tissue depths relative to a surface of the skin. The graphical data can be unique to a particular radiotherapy device 326 and associated X-ray tube 327.

As is known, a particular X-ray tube (e.g., X-ray tube 600) used for delivery of radiation therapy to a patient will have a radiation output profile which is determined by various factors. These factors can include minor variations in the manufacture of the X-ray tube and in the radiation filters 607 that are used. Accordingly, the radiation characteristic of a particular radiotherapy delivery component will generally be unique to each particular radiation therapy device or machine. For example, a Percentage Depth Dose ("PDD") plot 906 can be used to graphically show how much of a radiation dose from a particular radiation therapy machine will actually be delivered to skin tissue as a function of penetration depth. A PDD will vary in accordance with each radiotherapy system in accordance with minor variations in the X-ray tube and associated filters. Such a PDD characteristic is sometimes presented graphically. As will be appreciated, a radiation output profile such as PDD can be very important to a practitioner who needs to understand how applied radiation from the machine will interact with the tumor at various skin depths. In some scenarios, the PDD levels can be shown graphically as layers or rings 908a, 908b, 908c corresponding to the different radiation dose levels at different depths. The presentation of the PDD data in this way can allow a treatment specialist to more easily determine the amount of radiation which is to be applied to each portion of the cancerous cells 904.

Consequently, once a skin cancer has been imaged using the hybrid imaging methods described herein, it is advantageous to display the hybrid image (in two-dimensions or three-dimensions) to a treatment specialist together with a superimposed scaled graphical representation of the radiation dose profile (e.g., a PDD profile) 906 of a radiation therapy device which will actually be used to administer the radiation treatment. In this way, the treatment practitioner can visually evaluate the dose of radiation that will be delivered to various portions of the cancer as displayed, when using a particular radiation delivery device.

According to a further aspect, a graphical representation of the radiation dose profile can be included in the 3D representation of the radiation beam resulting from a particular shield pattern as described above. This graphic information can be combined with or overlaid on the hybrid image of the cancerous tissue as shown in FIG. 9 so that a proposed radiation treatment can be automatically evaluated by the RTP system. For example, a processor 330 associated with an RTP system 350 can evaluate whether all identified areas comprising cancerous skin cells will receive an adequate dose of radiation based on the foregoing. In some scenarios, the results of such evaluation can be communicated to a treatment specialist by highlighting or illuminating identified portions of the cancerous cells that will receive an inadequate dose of radiation. For example, such tissue areas can be highlighted in a different color to show the deficiency of the resulting 3D beam pattern. All of the foregoing information can be used by the treatment specialist to develop a suitable treatment plan in accordance with step 503 in FIG. 5.

Upon completion of disease assessment 502 and therapy planning 503, the process continues at 504 where image-guided radiotherapy treatment fraction is actually delivered. A radiotherapy component or device, such as component 220 from FIG. 2 or device 326 from FIG. 3, can be used to deliver treatment according to the treatment plan. Thus, the treatment plan can be read and interpreted and X-ray beam therapy can be delivered accordingly to the designated lesion. In this regard, the X-ray beam therapy is guided by the 3D imaging and dosimetry data from the treatment plan that was specifically created for the patient and the specific skin lesion to be treated.

In one arrangement, the components of the system 250 of FIG. 2 can be used to provide the image-guided radiotherapy treatment of step 504. The treatment head 206 and treatment applicators 307, 308 can be positioned over the patient's area to be treated utilizing the built-in video-laser positioning system 215, 217. The video-laser positioning system operates to align the treated area's video image with a low opacity snapshot of the previous treatment head 206 position together with crosshairs projected by laser 217 that are projected in both real-time and previous snapshot images. The system then ensures that the treated area's video image with laser crosshairs and the low opacity snapshot with the laser crosshairs are aligned together to the exact same position, which ensures an accurate and reproducible treatment head 206 positioning over the treated lesion. Once the treatment head 206 is in place, the user engages the system 250 to deliver the treatment fraction to the lesion. The timing, energy, and geometry of the beam are all guided by the image analysis, 3D tumor modeling, and the derived physics and dosimetry calculations and analysis.

For example, treatment can be provided in multiple, short fractionated treatment sessions. Each treatment fraction or session can be less than one (1) minute long while delivering a dose of approximately three hundred centigray (300 cGy) to approximately one thousand centigray (1000 cGy) per fraction. Depending on the prescribed total dose, the lesion can be treated with one or more fractions, such as around twelve (12) to around thirty (30) fractions. Additional or less fractions may be used.

A treatment series can include around five (5) to around thirty (30) fractions, per the protocol the physician prescribed for a particular lesion condition. Once the lesion is defined and identified, a treatment area is defined for the circumference. This circumference, in turn, can dictate the diameter of the applicator (such as applicators 207, 208 from FIG. 2 or applicator 609 from FIG. 6) that will be used. Generally, the selected applicator for treating a particular lesion circumference can be at least twenty percent (20%) larger in area and/or diameter of the lesion to be treated. The clinician can create a custom lead template or shield 652 that will be cut to the size and shape of the lesion with approximately a fifteen percent (15%) extra margin, in order to ensure that the entire malignant area will be impacted by the x-ray beam. All healthy cells that will be exposed to the x-ray beam will generally successfully recover and regenerate, while the malignant cells will go through an apoptosis from which they will not recover.

Figure 6:
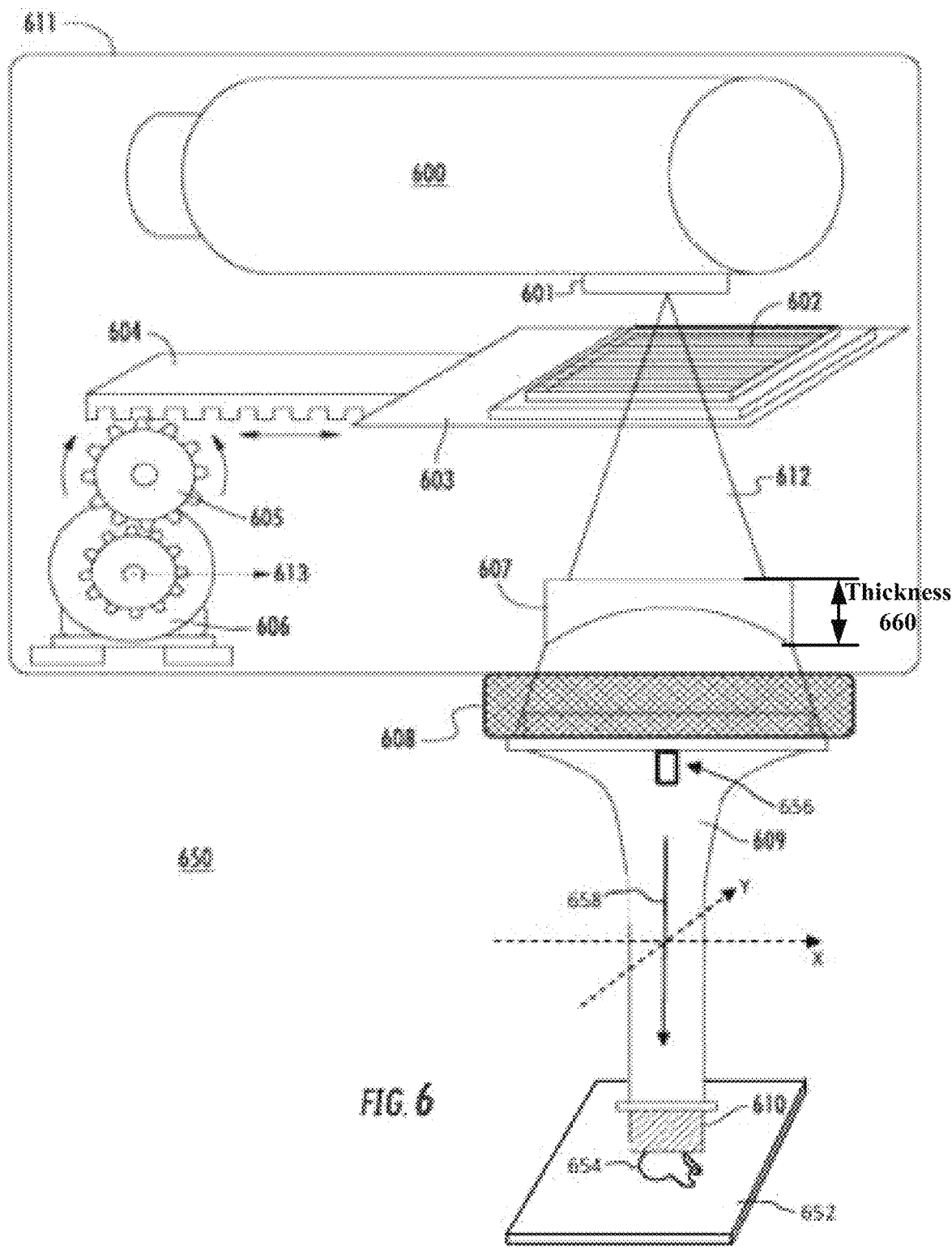
FIG. 6 is an illustration of an illustrative beam sensing component.

As shown in FIG. 6, the template or shield 652 can be placed over the lesion with the aperture or cutout 654 in the center of the treated area. The selected applicator 609 will be latched onto the x-ray tube head. The treatment system can be set with the pertinent energy level and time span of the treatment (e.g., approximately twenty (20) seconds to approximately forty (40) seconds), which are defined by vector tables, per the particular lesion's condition and fractionation scheme. The clinician can set the x-ray tube head vis-a-vis the applicator in position and aligned along a particular vector 658. Thereafter, the clinician can energize the system from the remote console, outside of the treatment room. The system can deliver the selected energy for the set time and can terminate treatment once the timers count to zero (0). The patient can be released and summoned for the next scheduled treatment session or fraction.

As will be discussed below, image-guided radiotherapy treatment step 504 can be repeated, but can be revised as needed. For instance, over the course of a treatment, a non-uniform shaped tumor may decrease in depth, width and overall size. Iterative treatments can be reduced in treatment size or intensity so that only the necessary amount of radiation is applied to as small a region as possible. In some scenarios, it can be advantageous to acquire further imaging data to characterize such changes in tumor depth, width and overall size. For example, the hybrid imaging methodology described herein can be used for this purpose. In some scenarios, additional or alternative imaging techniques can be used (such as LIDAR) to help to track the changes in the structure or anatomy of the tumor. The imaging data from these alternative methods can be combined or fused with imaging data acquired using other methods such as ultrasound and/or optical imaging methods as described.

The method 550 can then move on to the post treatment imaging phase. The post treatment imaging phase can be an iterative lesion imaging procedure that is completed after the previous imaging and assessment of the lesion. Post treatment imaging provides the ability to track and evaluate the therapy progression and healing process of the treated lesion during the fractionated therapy process. The interval of the lesion imaging is determined by the clinician according to the protocol illustrated in FIG. 7 and discussed further below.

At step 505, the treated area can again be imaged, as during the pre-treatment imaging stage. Thus, the actions and operations of step 500 can be repeated to obtain post-treatment structural and functional data for the tumor. The post treatment images and data of the treated lesion can be processed and a new fused 3D model of the tumor can be rendered in step 506. During step 506, the actions and operations of step 501 can be repeated.

The method 550 can then move to the treatment efficacy validation and analysis of steps 507 and 508, which provide for an iterative analysis of the lesion's topography and volume over time throughout the span of treatment and upon treatment completion, during the follow-up sessions. At step 507, the post treatment images and data from steps 505 and 506 can be assessed to determine how the legion responds to therapy in comparison to the anticipated healing rate, according the prescribed dosimetry and fractionation scheme of the treatment plan. Step 507 can include one or more of the actions or operations of step 502 to fully analyze a tumor or lesion.

As an example, if the newly acquired images and data indicates non-responsiveness, the treatment plan or other factors can be reviewed. In this regard, step 503 can be repeated where the treatment plan can be changed based on the post treatment imaging and assessment. On the other hand, if the newly acquired images and data indicates responsiveness, the treatment plan can be confirmed and treatment can progress. The steps provide an ongoing treated lesion assessment throughout the treatment and at its completion to evaluate the lesion evolution and its response to the therapy. The post treatment analysis can also be during the post-treatment follow-up sessions of the patient in order to document and validate or verify the full recovery and healing of the skin cancer lesion in the treated area.

In step 508, validation and confirmation of therapy efficacy and outcome can obtained. Step 508 can include image triangulation as a function of time and volume. By triangulating the 2D or 3D images, the size and shape of the tumor or lesion can be tracked. Also, volumetric analysis of the tumor over time can also be completed. The changes in the size, shape and volume of the tumor can be compared reviewed to determine effectiveness of the treatment, while factoring parameters of tumor transmutation and response to therapy. Thus, the clinician obtains an ongoing accurate assessment of the patient's response to therapy and can adjust the therapy if necessary in order to further optimize the patient's outcome. For instance, treatment session lengths or intensity can be decrease or increased. Step 508 can be completed locally by the clinician in a non-invasive manner, without any discomfort to the patient or the necessity for ancillary lab and pathology services.

At step 509, patient records can be stored and the method 550 completed. The records can include patient record data and images, results, and summary reports that illustrate the patient's disease state from procedure commencement to its ultimate conclusion. The records can be stored to local and networked record storage repositories.

Any of the steps can be repeated as needed. For instance, a tumor may require multiple treatment sessions before treatment is completed. The imaging steps, assessment and planning steps and the treatment steps may be repeated multiple times.

As all of these steps can be carried out with a single machine in a physician's office, this greatly cuts down the time, inconvenience and expense associate with diagnosis and treatment of non-melanoma skin cancer. Additionally, as it reduces or even removes the need for Mohs surgery, the patient's subsequent healing time and scarring is much reduced.

In certain configuration, the steps can be implemented via a workstation associated with the radiotherapy system. For example, computer 212 (as shown in FIG. 2) can be configured with a computer program to guide the user, such as a doctor, through the various steps of FIG. 5. Thus, from computer 212, the user can perform tumor imaging and modeling processes, diagnose based on the models obtained, and plan and carry out treatment plans using the models. In other configurations, the workstation can be deployed on a remote system. For example, on another computer connected over a network to the radiotherapy system.

Turning once again to FIG. 6, a solid state beam sensor and beam sensing component 650 (e.g., solid state beam sensor 313 and beam sensing component 312 of FIG. 3, or solid-state X-ray beam sensing component 102 of FIG. 1) can be provided. These components can be incorporated in an X-ray tube housing 611, such as the X-ray tube in treatment head 206 of FIG. 2.

The component or device 650 can include retractable support structure 603, 604 that can also be incorporated in X-ray tube housing 611. Also provided can be a x-ray imaging array detector, such as solid-state x-ray detector array 602, which is located between the X-Ray tube 600 with x-ray tube alignment 601, and a Bremsstrahlung beam-hardening aluminum filter 607. The solid-state detector array 602 that is mounted on the retractable support structure 603 can be utilized to sense the x-ray beam 612 output from the x-ray tube 600.

The retractable support structure 603 can move the solid-state detector array 602 between an X-ray testing position (as shown in FIG. 4A) and a non-testing position. In the non-testing position, the solid-state detector array 602 and/or the retractable support structure 603 is retracted or moved away from the field of emitted x-rays such that they do not absorb, block or otherwise interfere with radiation beams that are emitted from x-ray tube 600.

When the x-ray beam 612 is detected, the solid-state detector array 602 can sense characteristics of the radiation emitted from the x-ray tube 600. The detector array 602 can be used to generate a matrix-like image of the circumference of X-ray beam 612, together with the intensity of the x-ray beam's particles.

The x-ray imaging array detector can be a one-line array or a matrix array of solid state x-ray detectors that acquire and gather characteristics of the beam during the a check or testing procedure. One characteristic is the beam shape integrity, which validates that the x-ray tube output is indeed homogenous and without flaws. Another characteristic is the beam intensity that can be measured by centigray (cGy) or kilo-Volt (kV) units. Other characteristics sensed by the x-ray imaging array detector include the cross section or shape of the beam. The x-ray imaging array detector can also accurately measure the photons emitted from the x-ray tube 600. Further, the x-ray imaging array detector can also be used to determine whether the x-ray tube port 601 is properly aligned or if realignment is needed.

The collected data can be communicated to the beam sensing component, such as beam sensing component 312 of FIG. 3 that pre-processes the data. The pre-processed data can be communicated with a processor, such as processor 330, for further analysis and visualization. The solid state beam sensor and beam sensing component can be utilized as a daily quality control tool and for overall system diagnosis purposes. For instance, the solid state beam sensor and beam sensing component may detect a difference between the programmed radiation and what is output from the X-ray tube 600. Detection can allow for maintenance to ensure desired treatment dosages are delivered. Still further, testing can be automated before use such that the emitted x-rays and/or alignment of the x-ray tube port 601 is confirmed prior to each use.

The retractable support structure 603, 604 can include at least one motor or actuator 613 and positioning components 605, 606. The motor or actuator 613 can be controlled via a processor, such as processor 330 with the beam sensing component 314. The motor or actuator 613 can move the solid-state detector array 602 between the X-ray testing position and the non-testing position.

FIG. 6 also shows a removable treatment head or applicator 609 with tip 610. The removable head 609 and tip 610 can be used with a variety of radiotherapy devices (e.g., radiotherapy device 220 of FIGS. 2 and 326 of FIG. 3). The applicator 609 and tip 610 are both interchangeable. The interchangeability allows the x-ray device 650 to be modified to suit the treatment area and depth needed.

The applicator 609 can include, but are not limited to, applicators with lengths less than thirty centimeters (<30 cm). The tip 610 can include, but is not limited to, tips having a diameter between one centimeter (1 cm) and twelve and seven tenths centimeter (12.7 cm). For example, in some scenarios, a tip 610 with a diameter between one centimeter (1 cm) and seven and three tenth centimeter (7.3 cm) is used with a fifteen centimeter (15 cm) Source-to-Skin Distance ("SSD"). A tip 610 with a diameter between one centimeter (1 cm) and twelve and seven tenths centimeter (12.7 cm) is used with a twenty-five centimeter (25 cm) SSD.

The term "Source-to-Skin Distance ("SSD")", as used herein refers to the distance from a radiating isotropic source (e.g., x-ray tube 600 of FIG. 6) to the skin of the patient. The shorter the SSD the less attenuation (i.e., reduction in signal strength caused by signal transmission over a long distance) and the better the flow of photons emitted from the x-ray tube 600. Here, the SSD is controlled by use of the interchangeable applicator 609, i.e., the SSD is decreased by using a relatively short applicator and increased using a relatively long applicator.

As noted above, the present solution provides a means to deliver a required dose of radiation (e.g., 300, 500 or 700 centigray) to the patient in a significantly shorter period of time (e.g., ≤1 minute as opposed to >5 minutes) and for the same radiation energy (e.g., 50, 60, 70, 80, 90 or 100 kV). In this regard, a flow of desired photons emitted from the x-ray tube 600 is increased by (a) shortening the removable applicator 609 and (bi) using relatively thick filters 607 with normal dose rates or (bii) thin filters 607 with relatively high dose rates. Notably, a sufficient depth of penetration of radiation energy is provided in scenario (a), (bi) and scenario (a), (bii).

In some scenarios, it is desirable to have a depth of penetration of radiation energy greater than two millimeters (>2 mm). The increased depth is achieved using relatively thick or dense filters 607. However, the thick/dense filters cause radiation losses. The radiation losses are compensated for by shortening the removable applicator 609.

The applicator 609 may be shortened from fifteen, twenty-five or thirty centimeters (15/25/30 cm) to less than ten centimeters (<10 cm). The thick filters 607 can include, but are not limited to, aluminum filters having a thickness 660 greater than two and one tenth millimeters (>2.1 mm) and/or copper filters having a thickness 660 greater than five tenths millimeters (>0.5 mm). The normal dose rates can include, but are not limited to, less than one thousand centigray per minute (e.g., <1000 cGy/min). The thin filters 607 can include, but are not limited to, aluminum filters having a thickness 660 less than or equal to two and one tenth millimeters (≤2.1 mm). The high dose rates can include, but are not limited to, greater than one thousand centigray per minute (e.g., >1000 cGy/min).

In those or other scenarios, two or more filters are used for treating a patient. For example, an aluminum and a copper filter are used concurrently during a treatment process. The present solution is not limited to the particulars of this example.

Figure 7:
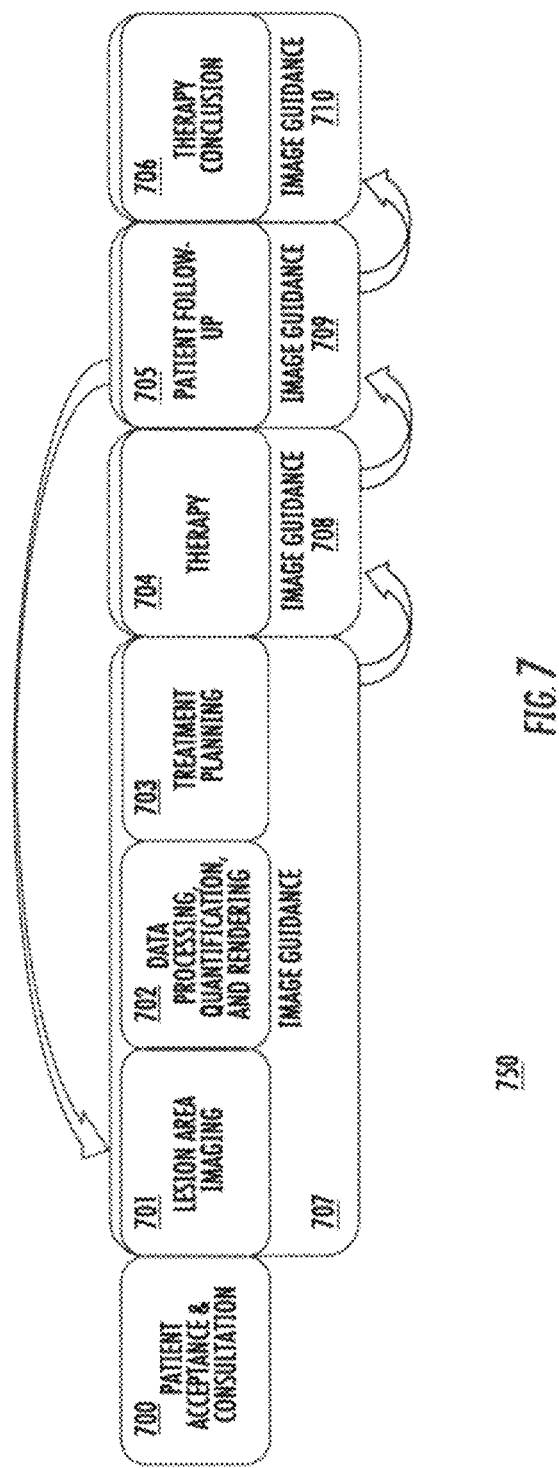
FIG. 7 is a flow diagram of a process of treating a patient.

FIG. 7 provides a flow chart of patient and treatment management protocol 750. When a patient first arrives at a doctor or clinician, the patient acceptance and consultation step 700 can occur. In this step, the patient is registered in the practice's workflow management system that can be integrated with a hybrid image-guided superficial radiotherapy system that can employ protocols such as DICOM and HL7, such as the system 350 illustrated at FIG. 3 or any suitable system.

With registration, the patient can be scheduled for the initial prognosis and consultation with the clinician. During initial prognosis and consultation, the patient can be scanned by an imaging device to obtain structural and functional information, as part of the image guidance phase 707. The scanning provides the clinician and the patient an assessment of any lesions and the disease state before making a decision on the recommended and preferred treatment path. The scanned lesion image data is then processed and reconstructed at step 702 to render the 2D image slices of the scanned area that contain the 2D cross-sections of the tumor. If desired, these images can be reviewed. The 2D tumor data can also converted to a 3D volumetric model and rendered to derive all the volumetric and physiological data of the tumor out of the scanned lesion, all for use in the next step.

Treatment planning step 703, uses the quantified data to calculate and generate a personalized treatment plan for the patient and the treated lesion.

Therapy can then commence at step 704, while imaging is still being applied 708 in varying intervals according to the clinician's and treatment plan's protocol to monitor and guide the course of the therapy throughout the prescribed fractions and entire treatment span.

Patient follow-up sessions 705 can be conducted to verify and monitor the full recovery of the treated lesion. As an example, follow-up sessions can be completed months or years after the last therapy session to monitor the area of a treated lesion. This stage is also being image-guided 709 with images obtained with a high frequency ultrasound device in order to add further validity to the treatment's outcome and to verify that indeed the lesion is completely cured and gone.

When the entire therapy sequence is complete at step 706, the patient data and all pertinent image-guidance data 710 is archived and submitted to the medical record management systems and the healthcare management systems. By generally the entire treatment process including non-invasive imaging as a substitute to invasive, time consuming, and expensive biopsies, the patient management protocol is being dramatically enhanced and improved, which offers benefits to all entities and parties involved, including the patient, the clinician, and the healthcare system as a whole.

The systems, methods and devices include broader applications beyond treating lesions or skin cancer. For instance, the systems, methods and devices can be utilized as intra operative radiotherapy in surgical environments to treat other cancers or lesions when their respective tumors are surgically removed. In addition to removal of a tumor, an excised area can imaged, analyzed and treated with the systems, methods and devices herein, such as treating an excised area with one or more twenty-one Gray (21 Gy) fractions before the patient is sutured.

In some arrangements, the systems, devices, methods and protocols can be employed for relatively superficial tumors that are not skin cancers, such as certain breast cancers, in which case the treatment head can include a surgical catheter for insertion beneath the skin, together with a small scale spherical treatment head.

It is important to note that the methods described above may incorporate any of the functionality, devices, and/or features of the systems described above, or otherwise, and are not intended to be limited to the description or examples provided herein.

Figure 8:
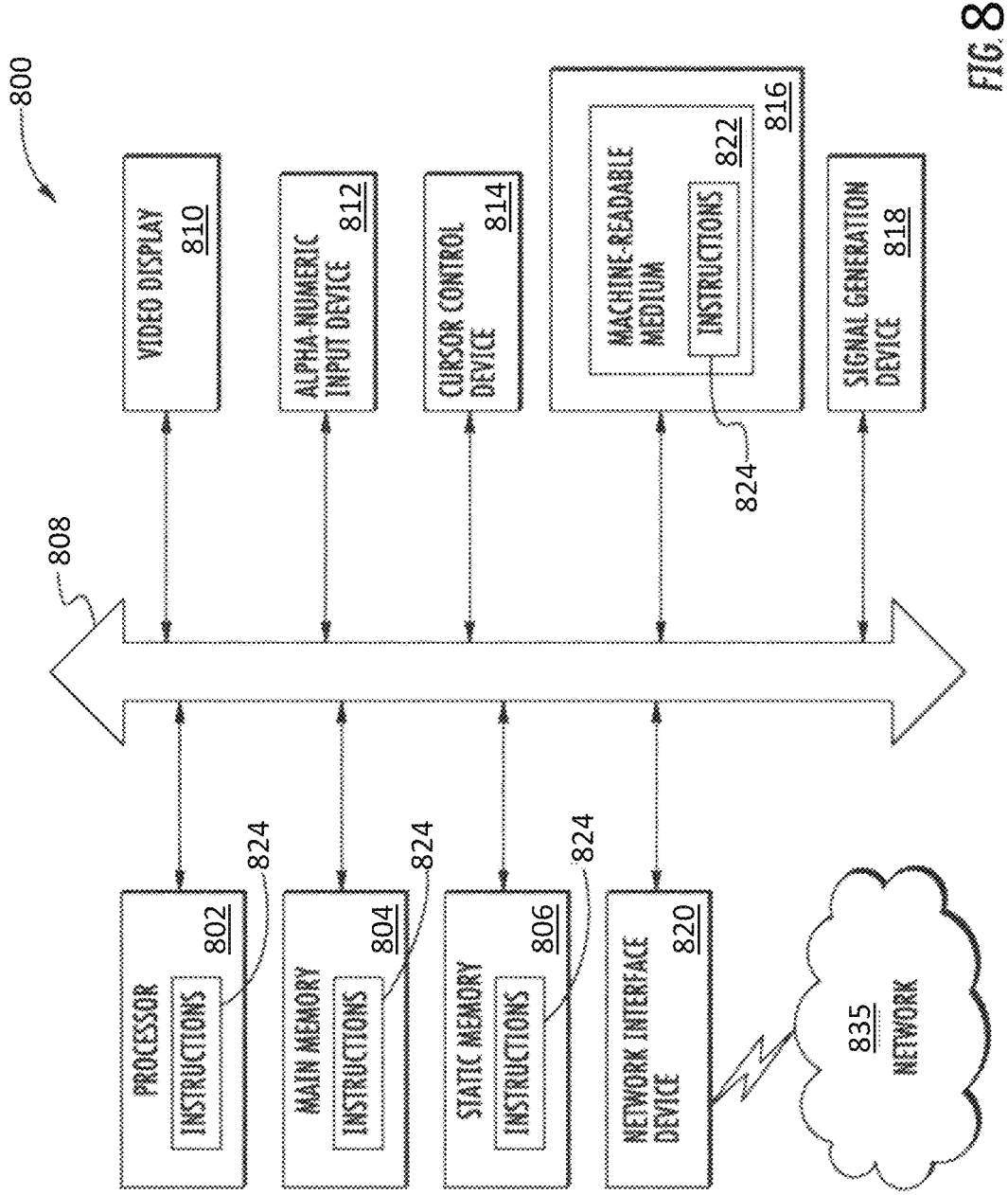
FIG. 8 is a diagrammatic representation of a machine in the form of a computer system within which a set of instructions, when executed, may cause the machine to perform any one or more of the methodologies discussed herein.

Referring now also to FIG. 8, at least a portion of the methodologies and techniques described can incorporate a machine, such as, but not limited to, computer system 800, or other computing device within which a set of instructions, when executed, may cause the machine to perform any one or more of the methodologies or functions discussed above. The machine may be configured to facilitate various operations conducted by the systems illustrated at FIGS. 3 and 4. For example, the machine may be configured to, but is not limited to, assist these systems by providing processing power to assist with processing loads experienced in the systems, by providing storage capacity for storing instructions or data traversing the systems, or by assisting with any other operations conducted by or within the systems.

In some scenarios, the machine operates as a standalone device. In some scenarios, the machine may be connected (e.g., using a network 835) via a network interface, such as network interface 328, to and assist with operations performed by other machines, such as, but not limited to, the radiotherapy device 326, central diagnostics component 312, the data repositories 304 and 305, the SRT control component 308 or the other devices and components of the system at FIG. 3, including any combination thereof. The machine may be connected with any component in the system at FIG. 3. In a networked deployment, the machine may operate in the capacity of a server or a client user machine in server-client user network environment, or as a peer machine in a peer-to-peer (or distributed) network environment. The machine may comprise a server computer, a client user computer, a Personal Computer ("PC"), a tablet PC, a laptop computer, a desktop computer, a control system, a network router, switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The computer system 800 may include a processor 802 (e.g., a CPU), a Graphics Processing Unit ("GPU"), a main memory 804 and/or a static memory 806, which communicate with each other via a bus 808. The computer system 800 may further include a video display unit 810 (e.g., a Liquid Crystal Display ("LCD"), a flat panel, a solid state display, or a Cathode Ray Tube ("CRT")). The computer system 800 may include an input device 812 (e.g., a keyboard), a cursor control device 814 (e.g., a mouse), a disk drive unit 816, a signal generation device 818 (e.g., a speaker or remote control) and a network interface device 820.

The disk drive unit 816 may include a machine-readable medium 822 on which is stored one or more sets of instructions 824 (e.g., software) embodying any one or more of the methodologies or functions described herein, including those methods illustrated above. The instructions 824 may also reside, completely or at least partially, within the main memory 804, the static memory 806, or within the processor 802, or a combination thereof, during execution thereof by the computer system 800. The main memory 804 and the processor 802 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various implementations of the present solution, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine readable medium 822 containing instructions 824 so that a device connected to the communications network 835 can send or receive voice, video or data, and to communicate over the network 835 using the instructions. The instructions 824 may further be transmitted or received over the network 835 via the network interface device 820.

While the machine-readable medium 822 is shown to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present disclosure.

The term "machine-readable medium" shall accordingly be taken to include, but not be limited to: solid-state memories such as a memory card or other package that houses one or more read-only (non-volatile) memories, random access memories, or other re-writable (volatile) memories; magneto-optical or optical medium such as a disk or tape; or other self-contained information archive or set of archives is considered a distribution medium equivalent to a tangible storage medium. In some scenarios, the machine readable storage medium may be a machine readable storage device or a computer readable device. Accordingly, the disclosure is considered to include any one or more of a machine-readable medium or a distribution medium, as listed herein and including art-recognized equivalents and successor media, in which the software implementations herein are stored.

Illustrative Workflow Management System

Figure 10:
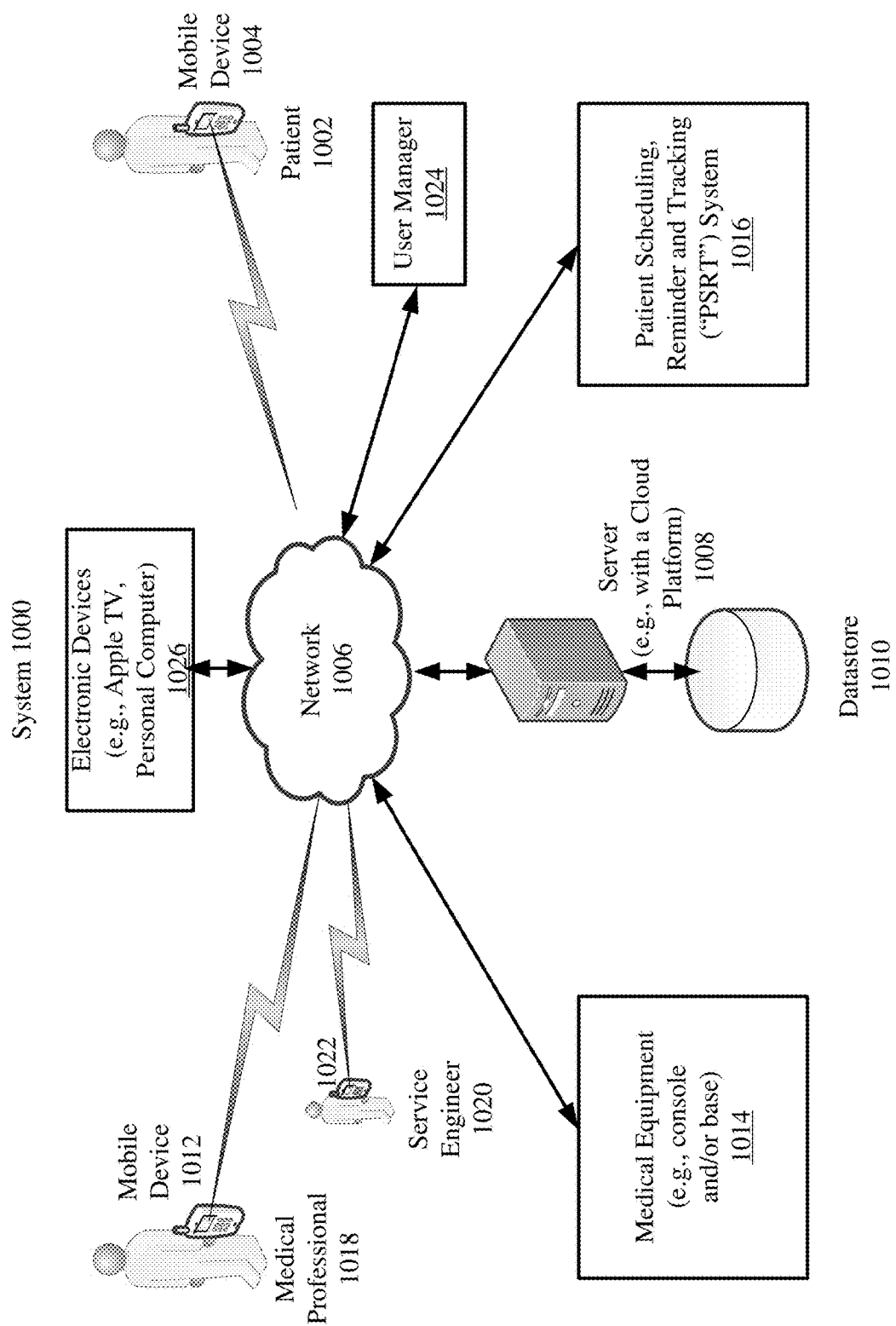
FIG. 10 is an illustration of an illustrative system implementing a method for mobile and wireless device workflow management in a medical context.

Referring now to FIG. 10, there is provided an illustration of an illustrative system 1000 implementing a method for mobile and wireless device workflow management in a medical context. System 1000 comprises hardware and/or software implementing the methods described herein. The hardware includes, but is not limited to, at least one processor. Processors are well known in the art, and therefore will not be described herein. Any known or to be known processor can be used herein without limitation. For example, a centralized or a distributed processor architecture can be employed.

In some scenarios, system 1000 comprises mobile devices 1004, 1012, 1022 (e.g., cell phones, smart phones, personal digital assistants, tablet computers, wearable devices, etc.), electronic devices 1026 (e.g., a smart television and/or a personal computer), a network 1006, medical equipment 1014, a server 1008, a datastore 1010 (e.g., a database), a Patient Scheduling, Reminder and Tracking ("PSRT") system 1016, and a user manager 1024. The network 1006 comprises the Internet, Intranet, and/or other known or to be known network. One or more of the listed components 1004-1016, 1022-1026 comprises a processor executing instructions implementing all or a portion of the methods described herein.

During operation, the medical equipment 1014 automatically performs system quality checks in response to being turned on. The medical equipment 1014 can be turned on manually by a person (e.g., a medical professional 1018 of FIG. 10). Additionally or alternatively, the medical equipment 1014 can be turned on/off without the assistance of a human. For example, an on/off switch of the medical equipment is remotely controlled by the server 1008. Various events can trigger a switch actuation by the server. These events can include, but are not limited to, a time of day, a system error or fault, and/or a user-software interaction by a physicist. A Rad Check is performed during system warm up by a radiation detector of the medical equipment. System quality checks and Rad Checks are well known in the art, and therefore will not be described herein. Any known or to be known system quality check and/or Rad check technique can be used herein without limitation. The data obtained from the system quality checks and the Rad check are processed by server 1008 and/or stored in the datastore 1010. The server 1008 may optionally process the Rad check results to see if appointments of patients to be treated on this day need to be rescheduled. Rescheduling may be needed if the medical equipment is experiencing a system fault or error which prevents its ability to provide treatment to patients. Such system faults and errors are known in the art, and therefore will not be described herein. If so, the server 1008 may perform operations to automatically cancel the patient(s) appointment and/or cause a rescheduling of the patient appointment(s) by the PSRT system 1016.

A physicist can be notified of a completed Rad check. At this time, the physicist accesses the results of the Rad check (stored in the datastore 1010) to see if a recalibration of the medical equipment 1014 is needed. A recalibration may be needed when there is a ±N% (e.g., 3%) deviation from predefined reference values. The recalibration can be performed manually by the physicist while at the site of the medical equipment. Alternatively, the recalibration can be triggered remotely by the physicist and performed by another person via the remote guidance of the physicist.

The distributed nature of the system 1000 allows patients to be treated with physicists having remote oversight. In this regard, system 1000 employs bi-directional electronic messaging between therapists/technicians of the medical equipment and the physicists who is remotely located from the medical equipment. For example, the physicist generates a message to the therapist/technician when (s)he reviews the patients electronic file via his(her) mobile device 1012 or personal computer 1026. The message is communicated from the physicist's electronic device 1012, 1026 to the server 1008 for storage in datastore 1010 so as to be associated with the patient's electronic file. When (a) the technician accesses the patient's electronic file at the time of treatment, the message is displayed on a display screen of the medical equipment. A notification can optionally be sent to the physicist's electronic device when the message is delivered to the medical equipment and/or presented to the technician. The present solution is not limited to the particulars of this example. In some scenarios, the physicist message(s) are generated and provided in real-time or near real-time while the patient is receiving treatment.

As shown in FIG. 10, each mobile device 1004, 1012, 1022 is respectively coupled to, being carried by or in the possession of a person 1002, 1018, 1020. For example, a mobile device 1004 is coupled to a patient 1004, while mobile device 1012 is coupled to a medical professional 1018 (e.g., a doctor, physicist, therapist, or dosimetrist) and mobile device 1022 is coupled to service engineer 1020. Each mobile device can include, but is not limited to, a mobile phone (as shown in FIG. 10), a smart phone, a smart watch, a portable computing device (e.g., a tablet or personal digital assistant), or a wearable communication device (e.g., an identification smart card). All of the listed devices are known in the art, and therefore will not be described herein.

The mobile device 1004 provides a means to identify the patient 1002. In some scenarios, a unique identifier for the mobile device 1004 is used to identify the patient 1002. The unique identifier can include, but is not limited to, a Media Access Control ("MAC") address. In other scenarios, a unique identifier assigned to this particular patient is used to identify the patient 1002. The unique identifier can include a numeric, alphabetic or alphanumeric sequence. The numeric sequence can be generated in accordance with a chaotic, random or pseudo-random number process. Any type of communication technology can be employed for acquiring the unique identifier and/or other information from the mobile device 1004. The communication technology can include, but is not limited to, cellular technology and/or short range communication technology (e.g., Bluetooth and/or Beacon).

During use of system 1000, operations are performed to detect when the patient 1002 arrives at a medical facility (e.g., enters a parking lot or a building). Such operations can involve: establishing a communications link between mobile device 1004 and network 1006; obtaining at least a unique identifier and location information from mobile device 1004; comparing the unique identifier to a plurality of unique identifiers stored in datastore 1010 to detect a match; determining the patient's 1004 name associated with the unique identifier stored in datastore 1010 that matches the unique identifier obtained from mobile device 1004; and/or determining the patient's location relative to a person, object or building of the medical facility based on the location information received from mobile device 1004.

The location information can include, but is not limited to, Geofencing information and/or Global Positioning System ("GPS") information. As generally understood in the art, GPS information may not be available while the mobile device 1004 resides in a building or closed structure. In this case, other techniques can be used to determine the patient's location in real time, such as a triangulation based technique, a proximity sensor (e.g., a beam break sensor) based technique and/or a beacon (e.g., iBeacon) based technique. In the beacon scenario, beacons are strategically placed around and/or in a parking lot and/or medical facility. The beacons have known locations. As such, the beacon identifiers can be communicated to the user manager 1024, server 1008 and/or PSRT system 1016 along with the unique identifier of the patient's mobile device 1004 for use in determining and/or tracking the patient's movement through the parking lot and/or medical facility.

Once the patient's name and/or location has/have been acquired, various operations may be performed to: notify a medical professional 1018 of the patient's arrival at the medical facility; track the person's movement through the medical facility; generate a map showing the patient's location and movement through the facility; and/or present the map to the medical professional 1018 and/or patient 1002. Additional information may also be presented to the medical professional 1018 and/or patient 1002 in addition to or as an alternative to the map. This additional information can include, but is not limited to, the patient's appointment time, the reason for the patient's appointment, and/or medical history information (e.g., type of cancer, location of cancer, total number of times the patient has received treatment for the cancer, etc.).

The unique identifier (of the mobile device 1004 or patient) and/or patient's name may also be used to acquire the patient's medical record and/or treatment plan from datastore 1010. In this regard, a server 1008 accesses datastore 1010 and retrieves the requisite data therefrom. In some scenarios, the server 1008 employs a cloud platform (e.g., Amazon Web Service ("AWS")). The medical record and/or treatment plan can be communicated to the medical professional 1018 via mobile device 1012 or other communication device 1026 (e.g., a desktop computer). Cryptography can be employed for some or all wired or wireless communications containing patient medical information. Any known or to be known cryptographic technique can be used herein without limitation.

The treatment plan may additionally or alternatively be provided to the medical equipment 1014 for use in configuring the same. In some scenarios, the medical equipment 1014 checks the results of a Rad check which was previously performed each time a treatment plan is provided thereto. Based on these results, the medical equipment 1014 may communicate with the server 1008 to obtain a recommendation for a different treatment protocol than that specified in the treatment plan. For example, the Rad check results indicate that the 70kV x-ray system components have been disabled (until recalibration) due to a greater than 3% deviation from predefined reference values. As such, the treatment cannot be given to the patient using the 70kV x-ray system components. However, the treatment can be provided to the patient using the 50kV x-ray system components. Accordingly, the server 1008 makes a recommendation for a different treatment protocol than that specified in the treatment plan. This recommendation is provided to the medical professional 1018 for review and approval via his(her) mobile device 1012 or personal computer 1026. Once approved, the recommended treatment protocol is provided to the medical equipment 1014 for use in configuring the same.

The medical equipment 1014 can include, but is not limited to, the ultrasound guided radio therapy treatment and diagnostic system 250 of FIG. 2. The medical equipment's configuration can be performed with or without human input in accordance with the treatment plan. In the case that human input is required for such configuration, the treatment plan may be used by the medical equipment to automatically confirm that the final configuration is consistent with the patient's treatment plan prior to providing any treatment (e.g., radiation) to the person (e.g., for treating cancer). The calibration can involve (a) transforming an operational mode/state of the medical equipment 1014 from a first operational mode/state to a second operational mode/state, and/or (b) transforming a parameter's value from a first value to a second value so that the medical equipment 1014 operates in accordance with the treatment plan. The first operational mode/state can be a mode/state in which radiation of a first dosage is to be applied to a patient for a first amount of time. In contrast, the second operational mode/state can be a mode/state in which radiation of a second dosage (different from the first dosage) is to be applied to a patient for a second amount of time (different from the first amount of time).

In some scenarios, treatment is not provided to the patient until his(her) identity is verified in the treatment room. This verification can be achieved using: SRC and/or beacon communications with his(her) mobile device 1004; fingerprint technology of the his(her) mobile device 1004 and/or the medical equipment 1014; and/or user-software interactions for inputting identifying information into the system via an input device of his(her) mobile device 1004, medical equipment 1014 and/or other computing device 1026. If the patient's identity is not verified, then the operational state of the medical equipment 1014 can optionally be changed so as to prevent treatment to the wrong person. For example, the operational state of the medical equipment is changed from an enabled state in which treatment can be provided to a lock-out state (or partially disabled state) in which at least a portion of its functions are disabled (e.g., until re-enabled or overridden by a medical professional or technician).

As the person receives treatment, system 1000 tracks the progress of such treatment. Information can be presented to the patient 1002 and/or medical professional 1018 specifying the treatment progress and/or status. For example, a scale is presented on a display screen of mobile device 1004 and/or mobile device 1012 showing a percentage indicating the treatment progress (e.g., 35% of the patient's treatment is completed). The patient's medical record is also (a) periodically or continuously updated as the patient receives treatment at the medical facility, and/or (b) updated upon treatment completion. The medical professional 1018 and/or his(her) assistants may be notified of treatment status and/or completion.

Also upon treatment completion, the PSRT 1016 is notified so that a next appointment is scheduled for the patient. The scheduling can be achieved with or without input from an employee of the medical facility. In this case, the patient is presented a Graphical User Interface ("GUI") on his(her) mobile device 1004 which facilitates appointment scheduling. The PSRT 1016 is also configured to periodically send the patient 1002 reminders of scheduled appointments via the mobile device 1004. The medical professional 1012 may also be notified of the patient's newly scheduled appointment so that (s)he can optionally modify the treatment plan prior to the patient's arrival at the medical facility for his(her) next treatment.

An application may be downloaded and executed on the patient's mobile device 1004 which allows the patient to quickly contact and/or communicate with the medical professional 1018 between treatment sessions (e.g., in the case of an emergency, or for prescription re-fills). The patient and medical professional can relay information therebetween via video, voice and/or text based communications. For example, the patient may send a textual message to the medical professional that (a) his(her) prescription needs to be re-filled soon so that an order can be placed with the requisite pharmacy in due course and/or (b) (s)he has just been emitted into a particular hospital.

System 1000 further comprises a user manager 1024 which has knowledge as to what events trigger certain operations (e.g., a patient's arrival at a medical facility triggers the provision of a notification to a medical professional). In some scenarios, each user is required to login to the user manager 1024 prior to being provided medical related services and/or information in real time (e.g., appointment notification and/or patient location/treatment nonfictions). The login may involve use of a username, password and/or biometrics.

For safety measures, the medical equipment 1014 can be configured to perform operations that are useful in determining if it is still satisfactorily calibrated at the end of each business day and/or the start of each business day (e.g., in response to being turned on). In this regard, the medical equipment 1014 is configured to detect status of various components and whether any of those components needs to be calibrated because its parameters fall outside an allowable range of values. A service engineer 1020 is notified about system faults, errors or other functionality on at least on an hourly, daily and/or weekly basis. Based on this information, the service engineer 1020 can determine when a calibration of the medical equipment 1014 is needed. Additionally or alternatively, the service engineer 1020 is only notified when the medical equipment 1014 experiences an error/fault or needs to be re-calibrated. The service engineer 1020 can receive electronic notifications via a mobile device 1022. The medical professional 1018 may also be provided some or all of the medical equipment functional-related information.

In some scenarios, the server 1008 is configured to analyze various data to learn and detect patterns therein. This data can include system check data, Rad check data, patient historical based data obtained by the medical equipment, and/or treatment related data obtained by other electronic devices. The learning is achieved using one or more machine learning algorithms. Machine learning algorithms are well known in the art, and therefore will not be described herein. Any known or to be known machine learning algorithm can be used herein without limitation. If a pattern is detected (e.g., based on the system check data and/or Rad check data) that indicates a potential system failure, a notification is sent to the service engineer 1020. In response to the notification, the service engineer 1020 may service the medical equipment in accordance with a recommended course of action determined based on the detected pattern. If a pattern is detected (e.g., based on patient historical data and/or other treatment related data) indicating that a particular outcome is likely given certain criteria, then the server 1008 may generate a recommended course of action for the treatment of a patient and/or a recommended treatment protocol for use in configuring the medical equipment.

The present solution has many advantages over conventional systems. For example, the present solution provides a means to increase the efficiency of, decrease the cost of, and decrease the time needed for patient treatment.

Figure 11:
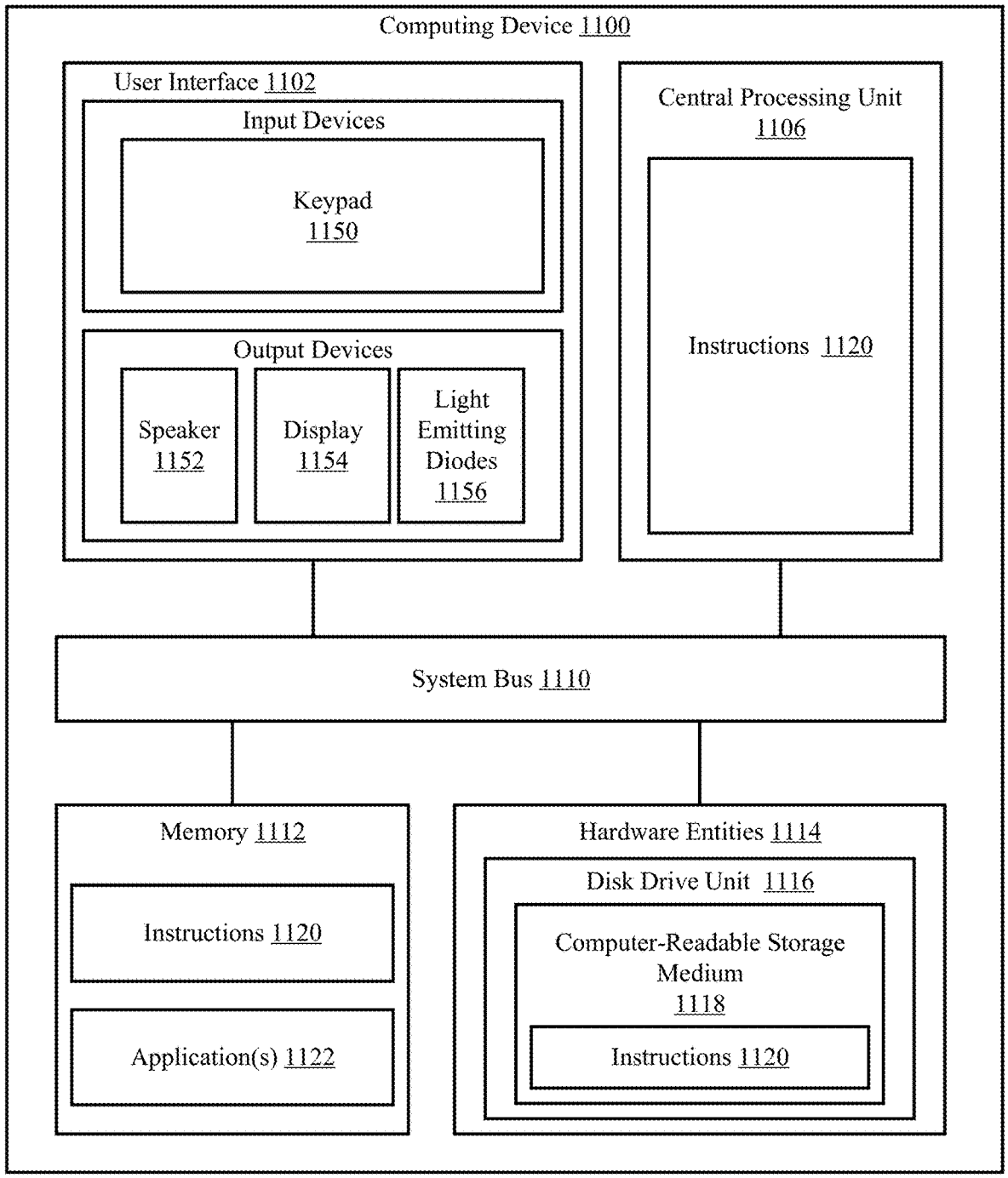
FIGS. 11 is a block diagram of an illustrative computing device.

Referring now to FIG. 11, there is provided an illustration of an illustrative architecture of a computing device 1100. Devices 1104, 1008, 1012, 1016, 1022 and/or 1026 of FIG. 10 can be the same as or similar to computing device 1100. As such, the following discussion of computing device 1100 is sufficient for understanding devices 1104, 1008, 1012, 1016, 1022, 1026 of FIG. 10.

Notably, the computing device 1100 may include more or less components than those shown in FIG. 11. However, the components shown are sufficient to disclose an illustrative embodiment implementing the present solution. The hardware architecture of FIG. 4 represents one embodiment of a representative server configured to facilitate inventory counts and management. As such, the computing device 1100 of FIG. 11 implements at least a portion of a method for workflow management in accordance with the present solution.

Some or all the components of the computing device 1100 can be implemented as hardware, software and/or a combination of hardware and software. The hardware includes, but is not limited to, one or more electronic circuits. The electronic circuits can include, but are not limited to, passive components (e.g., resistors and capacitors) and/or active components (e.g., amplifiers and/or microprocessors). The passive and/or active components can be adapted to, arranged to and/or programmed to perform one or more of the methodologies, procedures, or functions described herein.

As shown in FIG. 11, the computing device 1100 comprises a user interface 1102, a CPU 1106, a system bus 1110, a memory 1112 connected to and accessible by other portions of computing device 1100 through system bus 1110, and hardware entities 1114 connected to system bus 1110. The user interface can include input devices (e.g., a keypad 1150) and output devices (e.g., speaker 1152, a display 1154, and/or light emitting diodes 1156), which facilitate user-software interactions for controlling operations of the computing device 1100.

At least some of the hardware entities 1114 perform actions involving access to and use of memory 1112, which can be a Random Access Memory ("RAM"), a disk driver and/or a Compact Disc Read Only Memory ("CD-ROM"). Hardware entities 1114 can include a disk drive unit 1116 comprising a computer-readable storage medium 1118 on which is stored one or more sets of instructions 1120 (e.g., software code) configured to implement one or more of the methodologies, procedures, or functions described herein. The instructions 1120 can also reside, completely or at least partially, within the memory 1112 and/or within the CPU 1106 during execution thereof by the computing device 1100. The memory 1112 and the CPU 1106 also can constitute machine-readable media. The term "machine-readable media", as used here, refers to a single medium or multiple media (e.g., a centralized or distributed database, and/or associated caches and servers) that store the one or more sets of instructions 1120. The term "machine-readable media", as used here, also refers to any medium that is capable of storing, encoding or carrying a set of instructions 1120 for execution by the computing device 1100 and that cause the computing device 1100 to perform any one or more of the methodologies of the present disclosure.

In some scenarios, the hardware entities 1114 include an electronic circuit (e.g., a processor) programmed for facilitating the provision of workflow management in a medical context. In this regard, it should be understood that the electronic circuit can access and run a software application 1122 installed on the computing device 1100. The software application 1122 is generally operative to facilitate: a selective and/or remote control of medical equipment 1014 (e.g., to selectively and/or remotely be turned on and off); storing data obtained during system quality checks and Rad checks of the medical equipment; notifying a physicist of a completed system quality check and/or Rad check of the medical equipment; triggering a recalibration of the medical equipment in response to a user-software interaction by the physicist; facilitating the physicist's remote guidance of the medical equipment's recalibration; processing the system check data to see if appointments of patients to be treated on a given day need to be rescheduled; automatically canceling a patients appointment; automatically causing a rescheduling of a patients appointment; allowing remote access to a patient's electronic file (e.g., by the physicist); receiving a physicist's electronic message from a remote device; storing the physicist's electronic message so as to be associated with the patient's electronic file; causing the physicist's electronic message to be output from the medical equipment when the patient's electronic file is accessed at the time of treatment (e.g., by a technician); causing a notification message to be sent to the physicist when the medical equipment receives the physicist's electronic message and/or the medical equipment outputs the physicist's electronic message; facilitating a detection of a patient's arrival at a medical facility; notifying a medical professional of the patient's arrival at the medical facility; tracking the patient's movement through the medical facility; generating a map showing the patient's location and movement through the medical facility; causing the map and/or other information to be presented to the medical professional or patient; retrieving the patient's medical record and/or treatment plan from a datastore; communicating the patient's medical record and/or treatment plan to the medical professional's communication device, medical equipment, and/or other device(s); providing to the medical professional with a recommendation for a different treatment protocol than that specified in the treatment plan; receiving approval of the different treatment plan from the medical professional; causing the medical equipment to be reconfigured such that a patient is provided a treatment in accordance with the different treatment plan; remotely controlling the medical equipment such that the treatment is provided to the patient only when his(her) identity has been electronically verified; tracking the progress of the patient's treatment; causing treatment progress information to be presented from the medical equipment or other device; updating the patient's medical records to reflect the treatment progress; notifying at least the medical professional of the treatment status and/or completion; scheduling a next appointment for the patient; sending appointment reminders to the patient; notifying the medical professional of a patient's upcoming appointment; facilitating quick communications between patients and medical professionals between treatment sessions; and/or facilitating optimized calibrations and/or maintenance of the medical equipment. Other functions of the software application 422 will become apparent as the discussion progresses. Such other functions can relate to tag reader control and/or tag control.

Illustrative Method For Workflow Management In A Medical Context

Referring now to FIG. 12, there is provided a flow diagram of an illustrative method 1200 for workflow management in a medical context. Method 1200 begins with 1202 and continues with 1204 where a system quality check and/or a Rad check is(are) performed by medical equipment (e.g., medical equipment 250 of FIG. 2 and/or 1014 of FIG. 10). The data obtained during the system quality check and/or Rad check is communicated from the medical equipment to a computing device (e.g., server 1008 of FIG. 10), as shown by 1206. In 1208, the data is stored in a datastore (e.g., datastore 1010 of FIG. 10).

Thereafter in 1210, the computing device (e.g., server 1008 of FIG. 10) processes at least some of the data (e.g., the Rad check data) to determine if patient appointments need to be canceled. For example, if the Rad check data indicates that the medical equipment is experiencing a critical system failure, then a determination is made that patient appointments need to be canceled. Otherwise a determination is made that the patient appointments do not need to be canceled. The present solution is not limited to the particulars of this example.

If a determination is made that the patient appointments need to be canceled [1212:YES], then the computing device (e.g., server 1008 of FIG. 10) performs operations to cancel the patient appointments and/or cause the rescheduling of the patient appointments (e.g., by a PSRT system 1016 of FIG. 10), as shown by 1214. If a determination is made that the patient appointments do not need to be canceled [1212:NO], then 1216 is performed.

In 1216, the computing device (e.g., server 1008 of FIG. 10) performs operations to provide notification to a physicist (e.g., physicist 1018 of FIG. 10) of the completed system quality check and/or Rad check. A notification message is sent from the computing device (e.g., server 1008 of FIG. 10) to another electronic device (e.g., mobile device 1012 and/or electronic device 1026 of FIG. 10) being used by the physicist. The notification message is then output from the electronic device. In response to the notification message, the physicist accesses results of at least the Rad check to determine if a recalibration of the medical equipment is needed. If so, the physicist performs a user-software interaction for requesting recalibration of the medical equipment. In response to the user-software interaction, the electronic device communicates a medical equipment recalibration request to the computing device (e.g., server 1008 of FIG. 10). The medical equipment recalibration request is received by the computing device (e.g., server 1008 of FIG. 10) in 1218. In response to the medical equipment recalibration request, the computing device initiates a recalibration of the medical equipment. The recalibration can be performed by another person with the physicist's remote guidance as shown by 1222. This remote guidance is facilitated by the computing device (e.g., server 1008 of FIG. 10). In this regard, the computing device can act as an intermediary communication device between (a) the physicist's electronic device and the medical equipment, and/or (b) the physicist's electronic device and the other person's electronic device. The present solution is not limited in this regard. In other scenarios, the medical equipment recalibration is made remotely by the physicist without the assistance of another person.

Figure 12A:
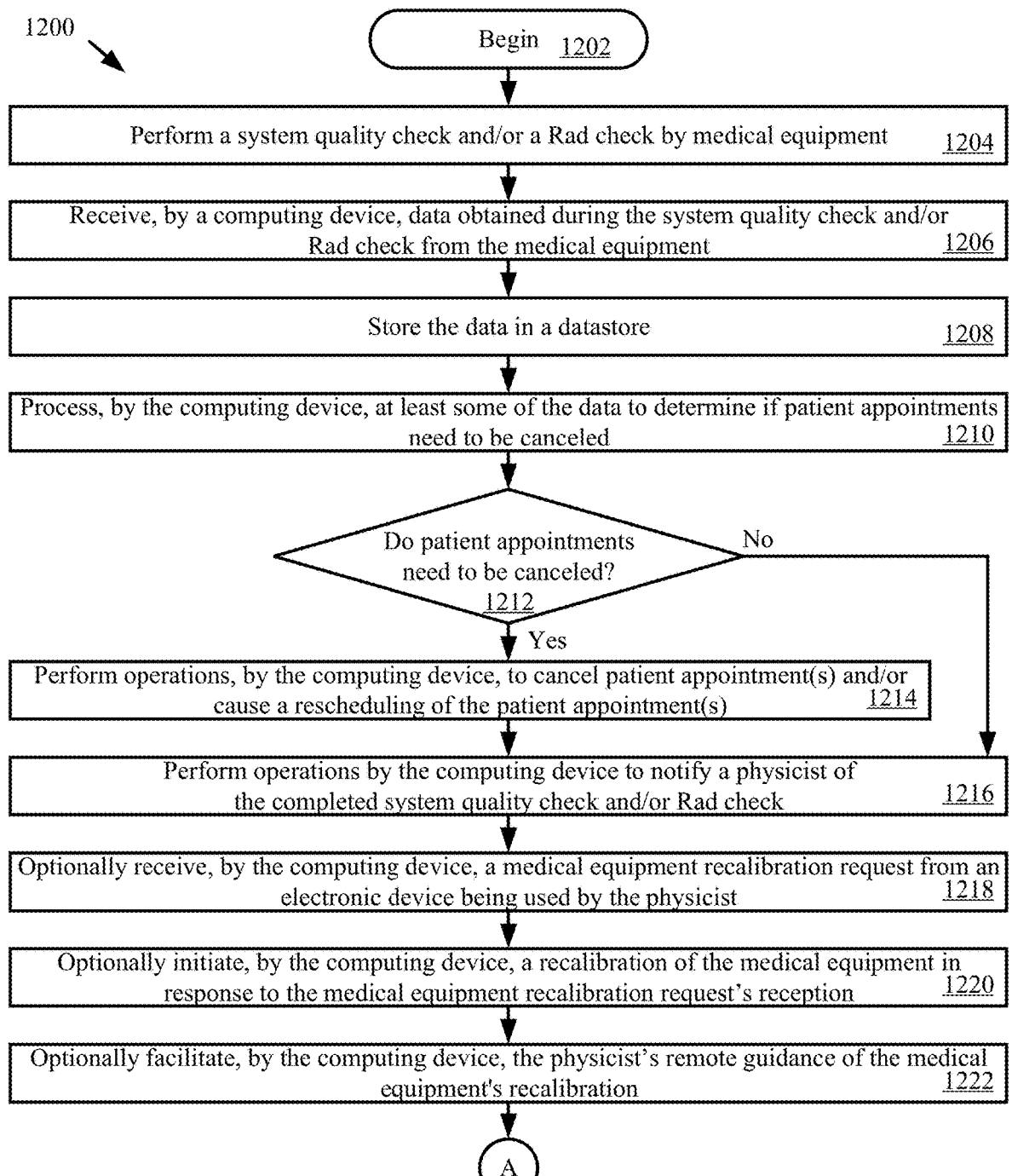
FIGS. 12A-12E (collectively referred to as "FIG. 12") provide a flow diagram of an illustrative method for workflow management in a medical context.
Figure 12B:
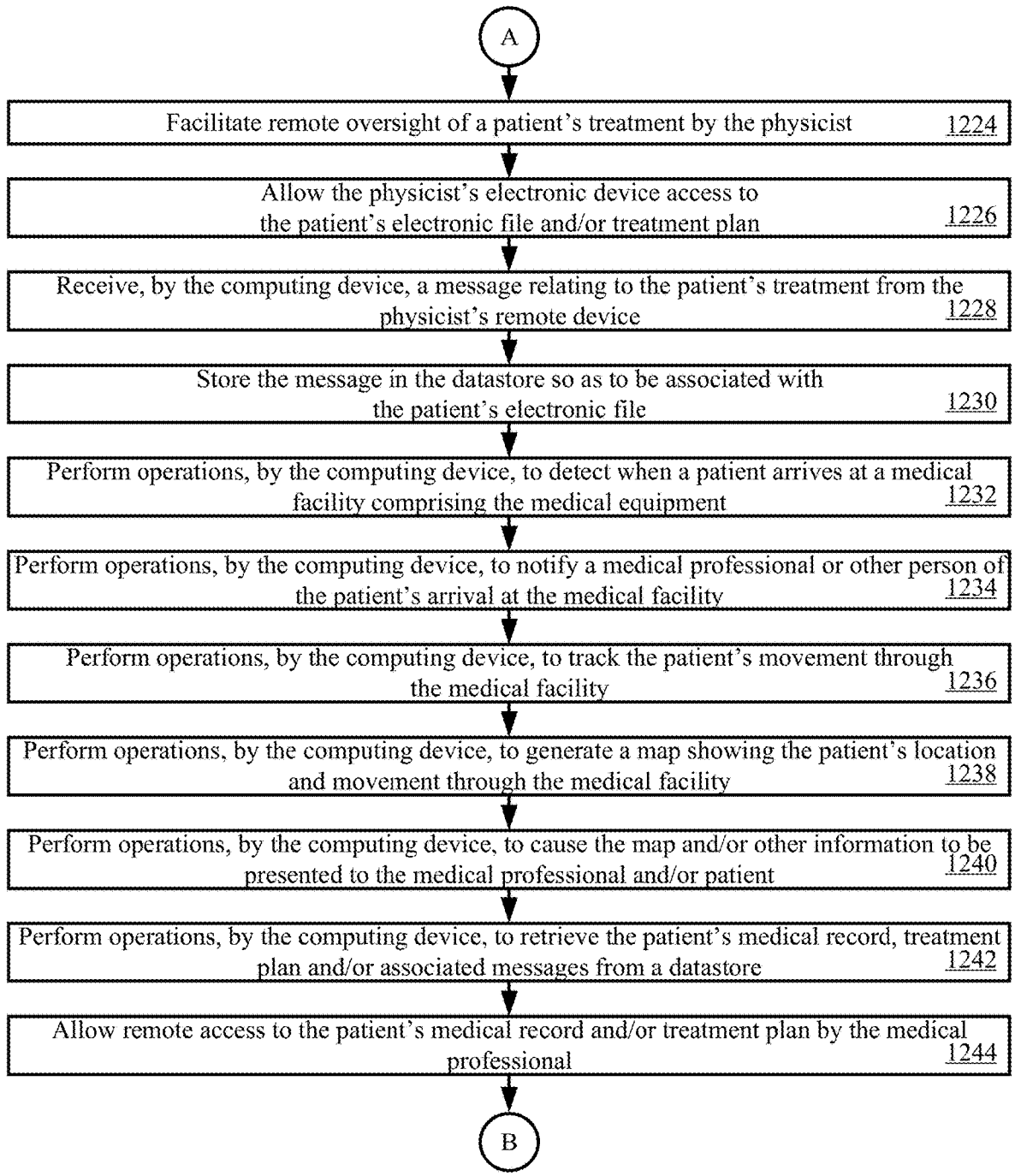

Upon completing 1216 or 1222, method 1200 continues with 1224 of FIG. 12B. As shown in FIG. 12B, 1224 involves facilitating remote oversight of a patient's treatment by the physicist. In this regard, the physicist's electronic device is allowed access to the patient's electronic file and/or treatment plan. When the physicist reviews the accessed information, (s)he performs user-software interactions with the electronic device for generating a message relating to the patient's treatment which is intended for a medical professional (e.g., technician or therapist 1018 of FIG. 10). The message is sent from the electronic device to the computing device (e.g., server 1008 of FIG. 10), as shown by 1228. The message is stored in the datastore (e.g., datastore 1010 of FIG. 10) so as to be associated with the patient's electronic file.

In 1232, the computing device (e.g., server 1008 of FIG. 10) detects when a patient arrives at a medical facility comprising the medical equipment. This detection can be made using electronic identification information and/or location information obtained from the patient's mobile device (e.g., mobile device 1004 of FIG. 10). When such a detection is made, the computing device performs operations in 1234 to notify a medical professional (e.g., medical professional 1018 of FIG. 10) or other person of the patient's arrival at the medical facility.

The patient's movement through the medical facility is tracked by the computing device (e.g., server 1008 of FIG. 10), as shown by 1236. A map is generated by the computing device in 1238 showing the patient's location and movement through the medical facility. The map and/or other information is presented to the medical professional and/or patient in 1240 via their mobile devices (e.g., mobile devices 1004, 1012 of FIG. 10).

In 1242, the computing device retrieves the patient's medical record, treatment plan and/or associated message(s) from the datastore (e.g., datastore 1010 of FIG. 10). The medical professional (e.g., medical professional 1018 of FIG. 10) is allowed access to the retrieved information, as shown by 1244. Subsequently, method 1200 continues with 1246 of FIG. 12C.

Figure 12C:
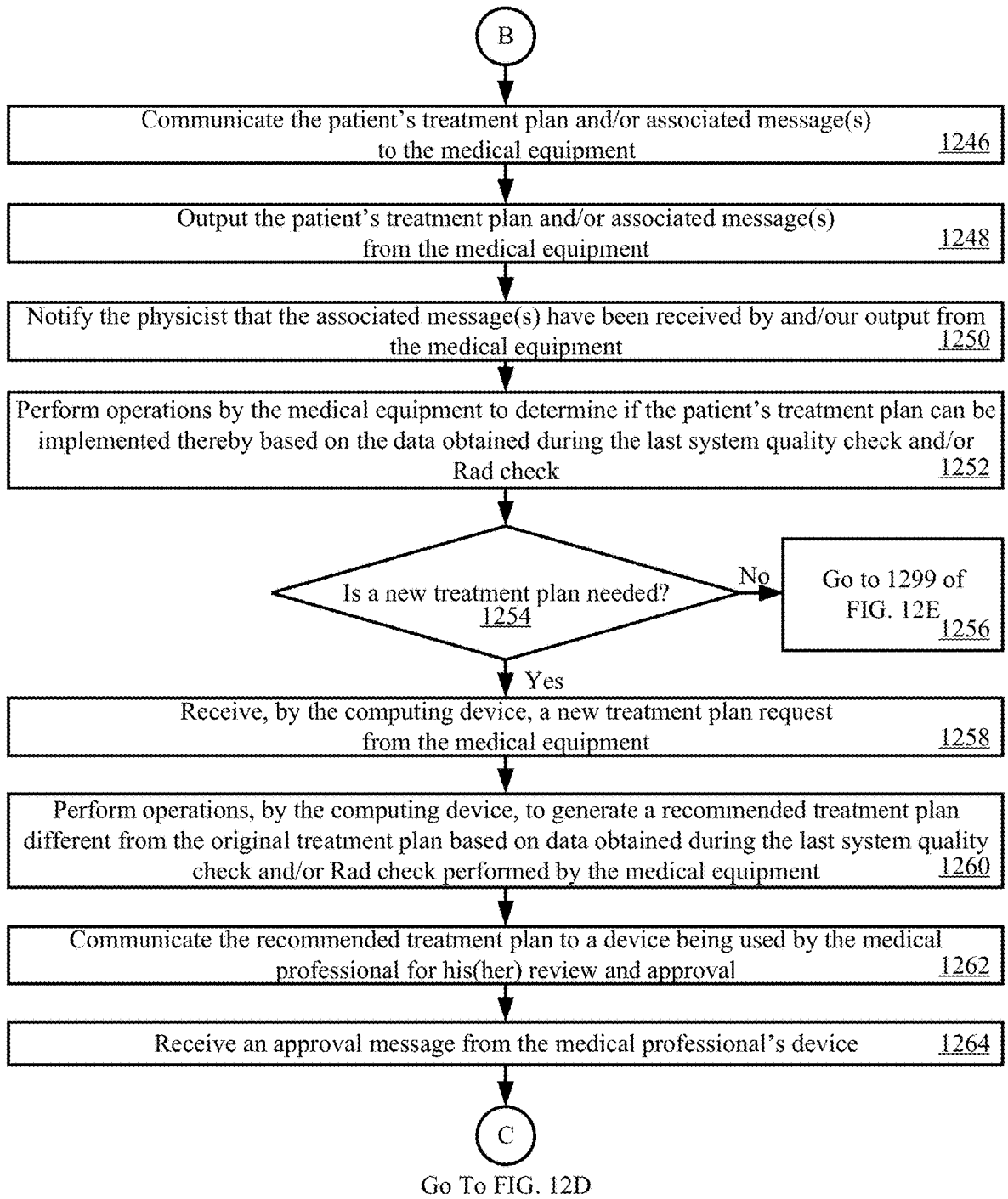
Figure 12D:
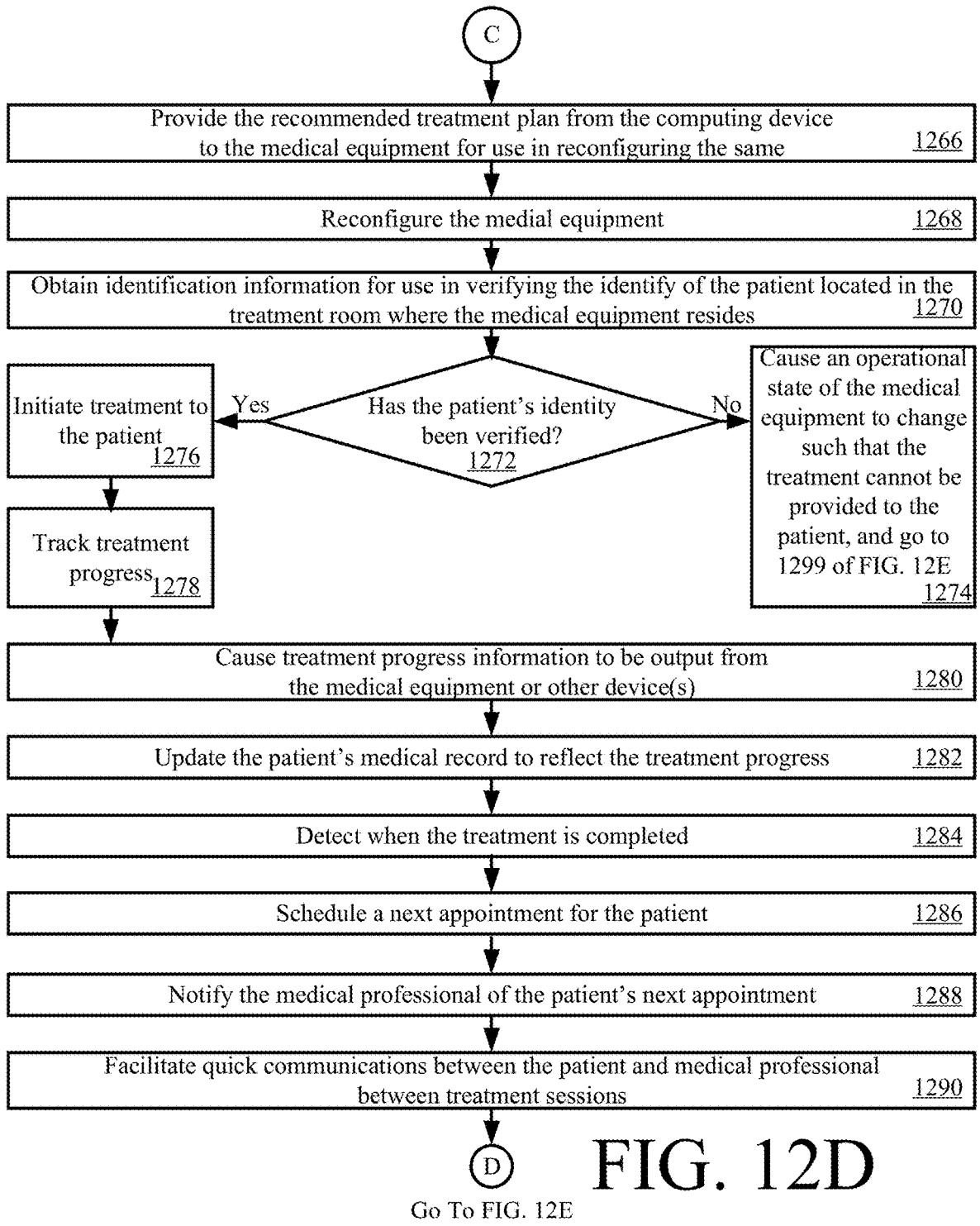

As shown in FIG. 12C, 1246 involves communicating the patient's treatment plan and/or associated message(s) to the medical equipment. The medical equipment outputs the patient's treatment plan and/or associated message(s) in 1248. Notably, the associated message(s) comprise(s) the physicist's message of previous 1226-1230 of FIG. 12B. The physicist is notified in 1250 when his(her) message has been received by and/or output from the medical equipment.

In 1252, the medical equipment performs operations to determine if the patient's treatment plan can be implemented thereby based on the data obtained during the last system quality check and/or Rad check. If so [1254:NO], then 1256 is performed where method 1200 continues with 1299 of FIG. 12E. In 1299, method 1200 ends or other processing is performed (e.g., return to 1204 of FIG. 12A).

If not [1254:YES], then 1258 is performed where the computing device (e.g., server 1008 of FIG. 10) receives a new treatment plan request from the medical equipment. In response to the request, the computing device generates a recommended treatment plan or procedure in 1260 based on data obtained during the last system quality check and/or Rad check performed by the medical equipment. The recommended treatment plan or procedure is different from that specified by the original treatment plan output from the medical equipment in 1248. The recommended treatment plan or procedure is communicated to a device being used by the medical professional for his(her) review and approval, as shown by 1262. This device can include, but is not limited to, the medical professional's mobile device (e.g., mobile device 1012 of FIG. 10). If the medical professional approves of the recommended treatment plan or procedure, then (s)he performs a user-software interaction with the device for generating an approval message. The approval message is sent from the device to the computing device (e.g., server 1008 of FIG. 10) in 1264. Thereafter, method 1200 continues with 1266 of FIG. 12D where the recommended treatment plan or procedure is provided to the medical equipment for use in reconfiguring the same. The medical equipment is reconfigured in 1268.

Next in 1270, identification information for the patient is obtained and communicated to the computing device (e.g., server 1008 of FIG. 10). The identification information can be obtained using: SRC and/or beacon communications with the patient's mobile device (e.g., mobile device 1004 of FIG. 10); fingerprint technology of the patient's mobile device or the medical equipment; and/or user-software interactions for inputting identifying information into the enterprise system via an input device of the patient's mobile device, the medical equipment, or other computing device (e.g., computing device 1026 of FIG. 10). The identification information is used by the computing device (e.g., server 1008 of FIG. 10) to verify the identity of the patient located in the treatment room where the medical equipment resides. The verification is achieved by comparing the obtained identification information with information stored in a database (e.g., database 1010 of FIG. 10) so as to be associated with the patient's electronic file. The patient's identity is verified when a match exists between the obtained identification information and the stored identification information.

If the patient's identity is not verified [1272:NO], then 1274 is performed where an operational state of the medical equipment is changed such that the treatment cannot be provided to the patient. For example, the operational state of the medical equipment is changed from an enabled state in which treatment can be provided thereby to a lock-out state (or a partially disabled state) in which at least a portion of its functions are disabled (e.g., until overridden or re-enabled by a medical professional or technician). Thereafter, method 1200 continues with 1299 of FIG. 12E where the method ends or other processing is performed.

If the patient's identity is verified [1272:YES], then 1276-1278 are performed where the treatment is initiated and treatment progress is tracked. The treatment progress information is communicated from the computing device to the medical equipment or other device(s) in 1280. Upon receipt, the treatment progress information is output from the medical equipment or other device(s). Also in 1282, the patient's medical record is updated to reflect the treatment progress.

When completion of the treatment is detected in 1284, actions are taken to schedule a next appointment for the patient. These actions can involve: communicating a first notification from the medical equipment (e.g., medical equipment 1014 of FIG. 10) to the computing device (e.g., server 1008 of FIG. 10) when a treatment is completed; communicating a second notification of treatment completion from the computing device to the PSRT system (e.g., PSRT system 1016 of FIG. 10); and initiating appointment scheduling operations of the PSRT system in response to the second notification. Appointment scheduling operations are well known in the art, and therefore will not be described herein. Any known or to be known appointment scheduling operations can be used herein without limitation.

Once the patient's next appointment has been scheduled, the medical professional is notified in 1288. This notification can be provided to the medical professional's device (e.g., mobile device 1012 of FIG. 10 or electronic device 1026 of FIG. 10) directly from the PSRT system or indirectly from the PSRT system via the computing device (e.g., server 1008 of FIG. 10). In response to the notification, the medical professional can modify the patient's treatment plan prior to the patient's arrival at the medical facility for his(her) next treatment.

In 1290, the enterprise system (e.g., system 1000) facilitates quick communications between the patient and medical professional between treatment sessions. Various types of communication technology can be used here. The communication technology includes, but is not limited to, video conference technology, electronic messaging technology, and/or phone technology.

Figure 12E:
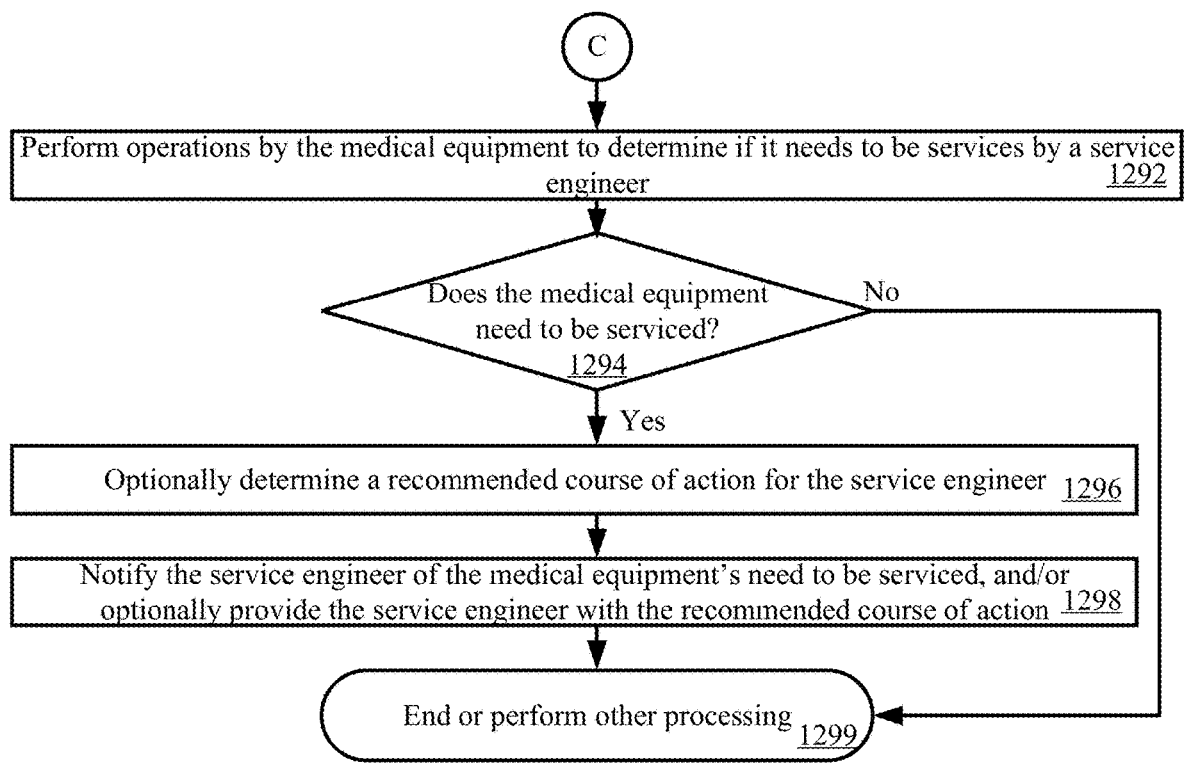

Referring now to FIG. 12E, method 1200 also involves performing operations to determine if the medical equipment needs to be serviced on a continuous basis or a periodic basis, as shown by 1292. This determination is made based on results of health checks, system quality checks and/or Rad checks performed by the medical equipment. Health checks are well known in the art, and therefore will not be described herein. The health checks can comprise the system quality checks and/or Rad checks. If a determination is made that the medical equipment does not need to be serviced [1294:NO], then 1299 is performed where method 1200 ends or other processing is performed.

In contrast, if a determination is made that the medical equipment does need to be serviced [1294:YES], then 1296-1298 are performed. 1296-1298 involve: optionally determining, by the computing device (e.g., server 1008 of FIG. 10), a recommended course of action for a service engineer (e.g., service engineer 1020 of FIG. 10); notifying the service engineer of the medical equipment's need to be serviced (e.g., via the service engineer's mobile device 1022 of FIG. 10); and/or optionally providing the service engineer with the recommended course of action. Subsequently, 1299 is performed where method 1200 ends or other processing is performed.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A method for treating a patient, comprising:
   producing, by a radiotherapy system, a fused model for a least a portion of a region of interest comprising a superficial portion of a patient's skin by combining (a) structural imaging data acquired using high frequency ultrasound and (b) functional imaging data acquired using optical imaging, wherein the fused model comprises at least two voxels assigned respective color values of a plurality of different color values that are associated with different tissue densities;
   assigning a disease type classification to the fused model based on at least the respective color values;
   generating a radiation treatment plan for the patient based on the fused model;
   storing the radiation treatment plan in a datastore;
   detecting, by a processor, an arrival of the patient at a medical facility using first information acquired from a first mobile device coupled to or in proximity to the patient;
   obtaining, by the processor, the radiation treatment plan for the patient from the datastore using the first information, the radiation treatment plan specifying a first treatment protocol for configuring medical equipment such that the medical equipment is placed in a first operational state for providing a radiation treatment to the patient;
   causing, by the processor, generation of a second treatment protocol different from the first treatment protocol based on machine learned information indicating a particular outcome is likely given a pattern detected in (i) historical medical record data for the patient and (ii) operational system check data for the medical equipment, the second treatment protocol including information for configuring the medical equipment such that the medical equipment is placed in a second operational state different than the first operational state; and
   causing, by the processor, a state of medical equipment to be transitioned from a first configurable operational state in which a radiotherapy treatment head has a first position to a second configurable operational state in which the radiotherapy treatment head has a second different position, in accordance with the second treatment protocol.

2. The method according to claim 1, wherein the first information comprises a unique identifier for the first mobile device or a unique identifier for the patient.

3. The method according to claim 1, further comprising communicating a notification message indicating the patient's arrival at the medical facility from the processor to a communication device coupled to or in proximity to a medical professional.

4. The method according to claim 1, wherein the first configurable operational state comprises a state in which radiation of a first dosage is to be applied to a person for a first amount of time, and the second configurable operational state comprises a state in which radiation of a second dosage different from the first dosage is to be applied to the person or another person for a second amount of time different from the first amount of time.

5. The method according to claim 1, further comprising tracking the patient's movement through the medical facility.

6. The method according to claim 5, further comprising generating a map showing the patient's location and/or movement through the medical facility.

7. The method according to claim 6, further comprising presenting the map to the patient and/or a medical professional.

8. The method according to claim 1, further comprising determining the person's location in the medical facility using beacons having known locations.

9. The method according to claim 1, further comprising automatically acquiring at least one of appointment information and medical related information for the patient from a remote datastore in response to the detection of the patient's arrival at the medical facility.

10. The method according to claim 9, further comprising presenting at least one of the appointment information and medical related information to the patient via the mobile device or a medical professional via a communication device coupled thereto or in proximity thereto.

11. The method according to claim 1, further comprising retrieving the patient's medical record from the remote datastore using the first information.

12. The method according to claim 1, wherein the medical equipment comprises an ultrasound guided radio therapy treatment and diagnosis system.

13. The method according to claim 1, further comprising performing operations by the computing device to track progress of the patient's treatment.

14. The method according to claim 1, further comprising (a) periodically or continuously updating the patient's medical record as the patient receives treatment at the medical facility or (b) updating the patient's medical record upon completion of the treatment.

15. The method according to claim 1, further comprising scheduling or reminding the patient of a next appointment.

16. The method according to claim 1, further comprising notifying a medical professional of the patient's next appointment so that the first or second radiation treatment plan is modified prior to the patient's arrival once again at the medical facility.

17. The method according to claim 1, further comprising detecting a status of the medical equipment and communicating information specifying the status to a communication device of a service engineer on an hourly, daily or weekly basis.

18. A system, comprising:
a radiotherapy system configured to
produce a fused model for a least a portion of a region of interest comprising a superficial portion of a patient's skin by combining (a) structural imaging data acquired using high frequency ultrasound and (b) functional imaging data acquired using optical imaging, wherein the fused model comprises at least two voxels assigned respective color values of a plurality of different color values that are associated with different tissue densities;
assigning a disease type classification to the fused model based on at least the respective color values; and
generate a radiation treatment plan for a patient based on the fused model;
a datastore configured to store the radiation treatment plan; and
a processor programmed to:
detect when a patient arrives at a medical facility using first information acquired from a first mobile device coupled to the patient;
obtain the radiation treatment plan for the patient from the datastore using the first information, the radiation treatment plan specifying a first treatment protocol for configuring medical equipment such that the medical equipment is placed in a first operation state for providing a radiation treatment to the patient;
cause generation of a second treatment protocol different from the first treatment protocol based on machine learned information indicating a particular outcome is likely given a pattern detected in (i) historical medical record data for the patient and (ii) operational system check data for the medical equipment, the second treatment protocol including information for configuring the medical equipment such that the medical equipment is placed in a second operational state different than the first operational state; and
cause a state of medical equipment to be transitioned from a first configurable operational state in which a radiotherapy treatment head has a first position to a second configurable operational state in which the radiotherapy treatment head has a second different position, in accordance with the second treatment protocol.

19. The system according to claim 18, wherein the first information comprises a unique identifier for the first mobile device or a unique identifier for the patient.

20. The system according to claim 18, wherein the processor is further programmed to communicate a notification message indicating the patient's arrival at the medical facility to a communication device coupled to or in proximity to a medical professional.

21. The system according to claim 18, wherein the first configurable operational state comprises a state in which radiation of a first dosage is to be applied to a person for a first amount of time, and the second configurable operational state comprises a state in which radiation of a second dosage different from the first dosage is to be applied to the person or another person for a second amount of time different from the first amount of time.

22. The system according to claim 18, wherein the processor is further programmed to track the patient's movement through the medical facility.

23. The system according to claim 22, wherein the processor is further programmed to generate a map showing the patient's location and/or movement through the medical facility.

24. The system according to claim 23, wherein the processor is further programmed to present the map to the patient and/or a medical professional.

25. The system according to claim 18, wherein the processor is further programmed to determine the person's location in the medical facility using known locations of beacons.

26. The system according to claim 18, wherein the processor is further programmed to acquire at least one of appointment information and medical related information for the patient from the datastore in response to the detection of the patient's arrival at the medical facility.

27. The system according to claim 26, wherein the processor is further programmed to cause at least one of the appointment information and medical related information to be presented to the patient via the mobile device or a medical professional via a communication device coupled thereto or in proximity thereto.

28. The system according to claim 18, wherein the medical equipment comprises an ultrasound guided radio therapy treatment and diagnosis system.

29. The system according to claim 18, wherein the processor is further programmed to track progress of the patient's treatment.

30. The system according to claim 18, wherein the processor is further programmed to (a) periodically or continuously update the patient's medical record as the patient receives treatment at the medical facility or (b) update the patient's medical record upon completion of the treatment.

31. The system according to claim 18, wherein the processor is further programmed to schedule or remind the patient of a next appointment.

32. The system according to claim 18, wherein the processor is further programmed to notify a medical professional of the patient's next appointment so that the first or second radiation treatment plan is modified prior to the patient's arrival once again at the medical facility.

33. The system according to claim 18, wherein the processor is further programmed to detect a status of the medical equipment and communicate information specifying the status to a communication device of a service engineer on an hourly, daily or weekly basis.

* * * * *